Figure 1:
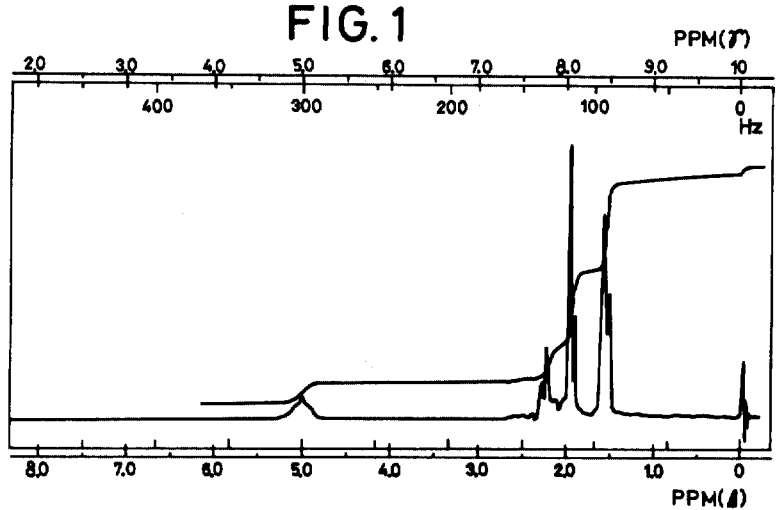

United States Patent [19]

Fujita et al.

[11] 4,028,385

[45] June 7, 1977

[54] PROCESS FOR PREPARING STEREOSPECIFIC FARNESYLACETIC ACID AND ESTER THEREOF

[75] Inventors: Yoshiji Fujita, Kurashiki; Yoshiaki Omura, Okayama; Takashi Nishida; Kazuo Itoi, both of Kurashiki, all of Japan

[73] Assignee: Kuraray Co., Ltd., Kurashiki, Japan

[22] Filed: Aug. 18, 1975

[21] Appl. No.: 605,455

[30] Foreign Application Priority Data

Sept. 2, 1974 Japan ............................ 49-100631
Sept. 2, 1974 Japan ............................ 49-100632
Sept. 2, 1974 Japan ............................ 49-100633
Sept. 2, 1974 Japan ............................ 49-100634
Sept. 2, 1974 Japan ............................ 49-100635

[52] U.S. Cl. ...................... 260/410; 260/410.9 R; 260/4.13; 260/631.5
[51] Int. Cl.² ...................... C11C 3/02; C11C 1/00
[58] Field of Search ............ 260/410, 410.9 R, 413, 260/631.5, 587

[56] References Cited

UNITED STATES PATENTS

| 2,848,502 | 8/1958 | Surmatis | 260/631.5 |
| 3,082,260 | 3/1963 | Tedeschi | 260/638 Y |
| 3,154,570 | 10/1964 | Adami | 260/419.9 R |
| 3,928,403 | 12/1975 | Fujita | 260/410.9 R |

OTHER PUBLICATIONS

Bates et al., J. Org. Chem. 28, 1086 (1963).

Primary Examiner—Winston A. Douglas
Assistant Examiner—John F. Niebling
Attorney, Agent, or Firm—Flynn & Frishauf

[57] ABSTRACT

A process for preparing stereospecific farnesylacetic acid and ester thereof by rectifying a mixture of $\Delta^{4,8}$-trans- and $\Delta^4$-cis-$\Delta^8$-trans-farnesylacetic acids or esters thereof or $\Delta^{4,8}$-trans- and $\Delta^4$-cis-$\Delta^8$-trans-farnesylacetic acid or esters thereof or a mixture of four isomers of the said farnesylacetic acids or esters thereof.

15 Claims, 21 Drawing Figures

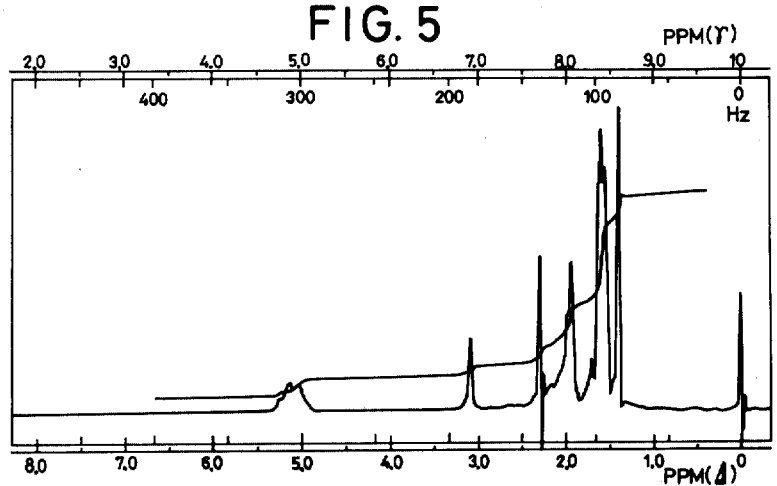
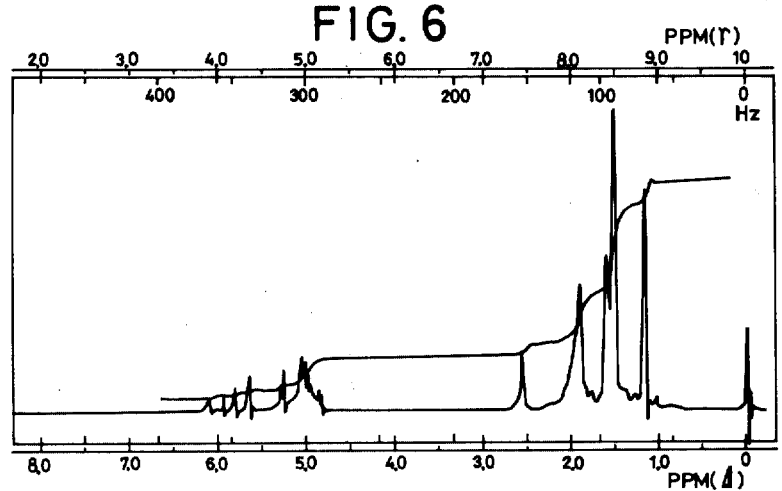

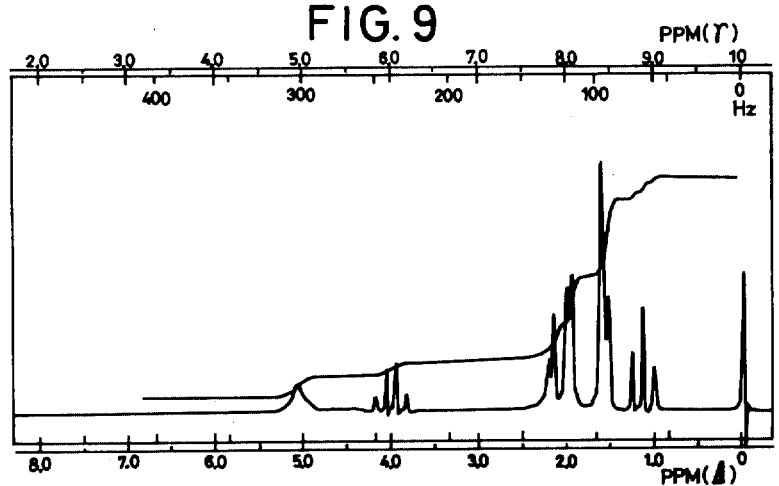
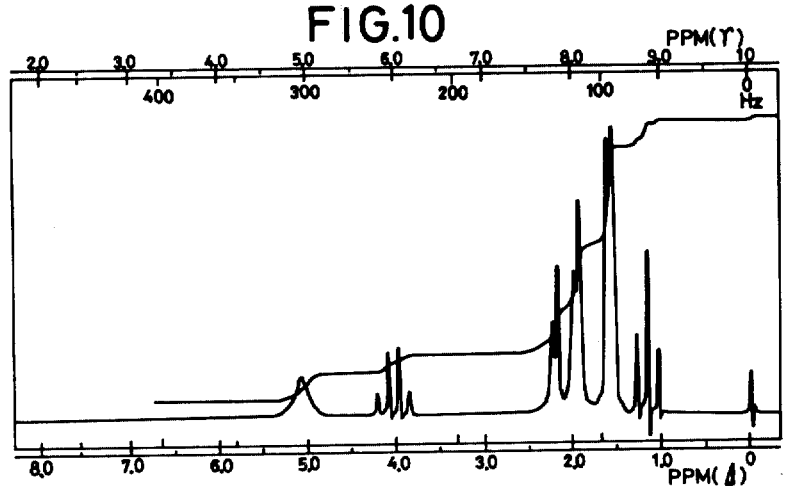

PROCESS FOR PREPARING STEREOSPECIFIC FARNESYLACETIC ACID AND ESTER THEREOF

This invention relates to a process for preparing a stereo-specific farnesylacetic acid or its ester. Particularly, this invention relates to a process for preparing, respectively, $\Delta^4$-cis-$\Delta^8$-trans-, $\Delta^{4,8}$-trans-, $\Delta^4$-trans- $\Delta^8$-cis- and $\Delta^{4,8}$-cis-farnesylacetic acids or esters thereof. More particularly, this invention relates to a process for preparing $\Delta^{4,8}$-trans-farnesylacetic acid or its ester. The above stereo-specific farnesylacetic acids or esters thereof are represented by the following formula (1):

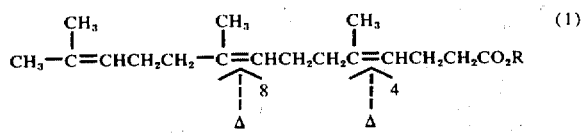

wherein R represents hydrogen atom, an alkyl, alkenyl, alkynyl, cycloalkyl, cycloalkenyl, aryl, aralkyl, aralkenyl or heterocyclic radical having not more than 20 carbon atoms.

Farnesylacetic acid esters are valuable compounds which are employed as medicines having anti-ulcer activity and also as perfumes.

As reported by E. Adami et al. in Med. Exptl., 7, 171 (1962) and J. Med. Chem., 6, 457 (1963), the farnesylacetic acid or its esters having the above formula (1) in case where R represents a ethyl group, allyl group, propargyl group, cyclohexyl group, geranyl group or farnesyl group, can show anti-ulcer activity but those wherein R represents a methyl group, propyl group, butyl group, isoamyl group or lauryl group do not show any anti-ulcer activity, while their activities may vary depending upon stereostructure of the double bonds at the $\Delta^4$-position and the $\Delta^8$-position therein.

The farnesylacetic acid and esters thereof having the above formula (1) have four stereoisomers, respectively. More specifically, they involve $\Delta^{4,8}$-cis-form, $\Delta^4$-trans- $\Delta^8$-cis-form, $\Delta^4$-cis- $\Delta^8$-trans-form and $\Delta^{4,8}$-trans-form.

In practice, these isomers have different physical and physiological properties and, when used as a medicine, their respective single forms are preferable. Such single forms are frequently required for the purpose of identification of a substance and of a chemical reagent.

For obtaining these isomers in pure single forms, there may be mentioned either of a stereospecific synthesis method or a separation method of a resultant mixture. The former has drawbacks of considerably complicated procedures and expensive reagents to be applied and, accordingly, this method has been at present regarded as industrially unavailable. Under these circumstances, the latter are being studied in the art.

For separation of these isomers, there has been proposed solely a separation method of farnesylacetic acid geraniol ester as reported by G. Pala et al, in Helv. Chim. Acta., 53, 1827 (1970). It is not feasible to separate farnesylacetic acid geraniol ester by distillation or gas chromatography and a column chromatography technique with silver nitrate should be applied. Such methods are suitable for separation of a small amount of a test sample, but not for industrial treatment of a large amount of a mixture. Then, as a result of our extensive studies in order to find out an industrially applicable separation method, we have completed the present invention.

In general, separation of cis-form and trans-form by means of distillation is suitable for separating a mixture of nerol and geraniol as reported by R. B. Bates et al. in J. Org. Chem., 28, 1086 (1963), but this separation method has been considered inefficient for its application to such high molecular compounds as farnesol et al. Therefore, it is natural to consider that this separation method is much more difficult for its application to such compounds of high boiling point as the above compounds (1) of formula.

However, we have unexpectedly found that the above compounds (1), only where R is a hydrogen atom, a lower alkyl group, a cycloalkyl group, a lower alkenyl group or a cycloalkenyl group, can be relatively easily separated into their respective isomers by means of rectification, on condition that the compounds comprise not a mixture of the above-mentioned four isomers but a mixture of $\Delta^{4,8}$-cis-form and $\Delta^4$-trans- $\Delta^8$-cis-form or of $\Delta^4$-cis- $\Delta^8$-trans-form and $\Delta^{4,8}$-trans-form and also that the above mixtures of respective two isomers can be easily synthesized, starting from the cis- and trans-forms of geranylacetone. Upon the above findings, we have completed the present invention.

The cis- or trans-form of geranyl acetone which may be employed as a starting material in the process of this invention may be a stereospecifically synthesized one, but it is generally practical to separate the forms from a mixture of the cis- and trans-forms.

For separation of a mixture of cis-geranylacetone and trans-geranylacetone are proposed a semicarbazone-recrystallization method reported by O. Isler et al. in Helv. Chim. Acta., 39, 897 (1956), a lower temperature crystallization method reported by O. Isler et al. in ibid. 43, 1745 (1960) and so on. However, industrially easy separation can be preferably accomplished by means of the rectification method which we have found.

There have been suggested various methods wherein $\Delta^8$-cis, $\Delta^4$-cis- and-trans-farnesylacetic acids and their esters or $\Delta^8$-trans, $\Delta^4$-cis- and trans-farnesylacetic acids and their esters are derived from the so obtained cis- or trans-form of geranylacetone. For instance, there are mentioned the following methods.

a. Wittig reaction of the geranylacetone with γ-bromobutyric acid ester,
b. condensation of farnesyl bromide with diethyl malonate and subsequent hydrolysis and decarboxylation as reported by G. Pala et al. in Helv. Chim. Acta., 53, 1827 (1970),
c. condensation of farnesyl bromide with acetoacetic acid ester, heating in an alcohol in the presence of sodium alkoxide and subsequent deacetylation with barium hydroxide as reported by E. Adami et al. in J. Med. Chem., 6, 457 (1963),
d. heating nerolidol and orthoacetic acid ester in the presence of an acidic catalyst, as disclosed in our co-pending Japanese Pat. Application No. 79448/1973 (U.S. Ser. No. 487,043), now U.S. Pat. No. 3,928,403.

However, the most preferable method for mass production in industrial scale is illustratively shown by the following.

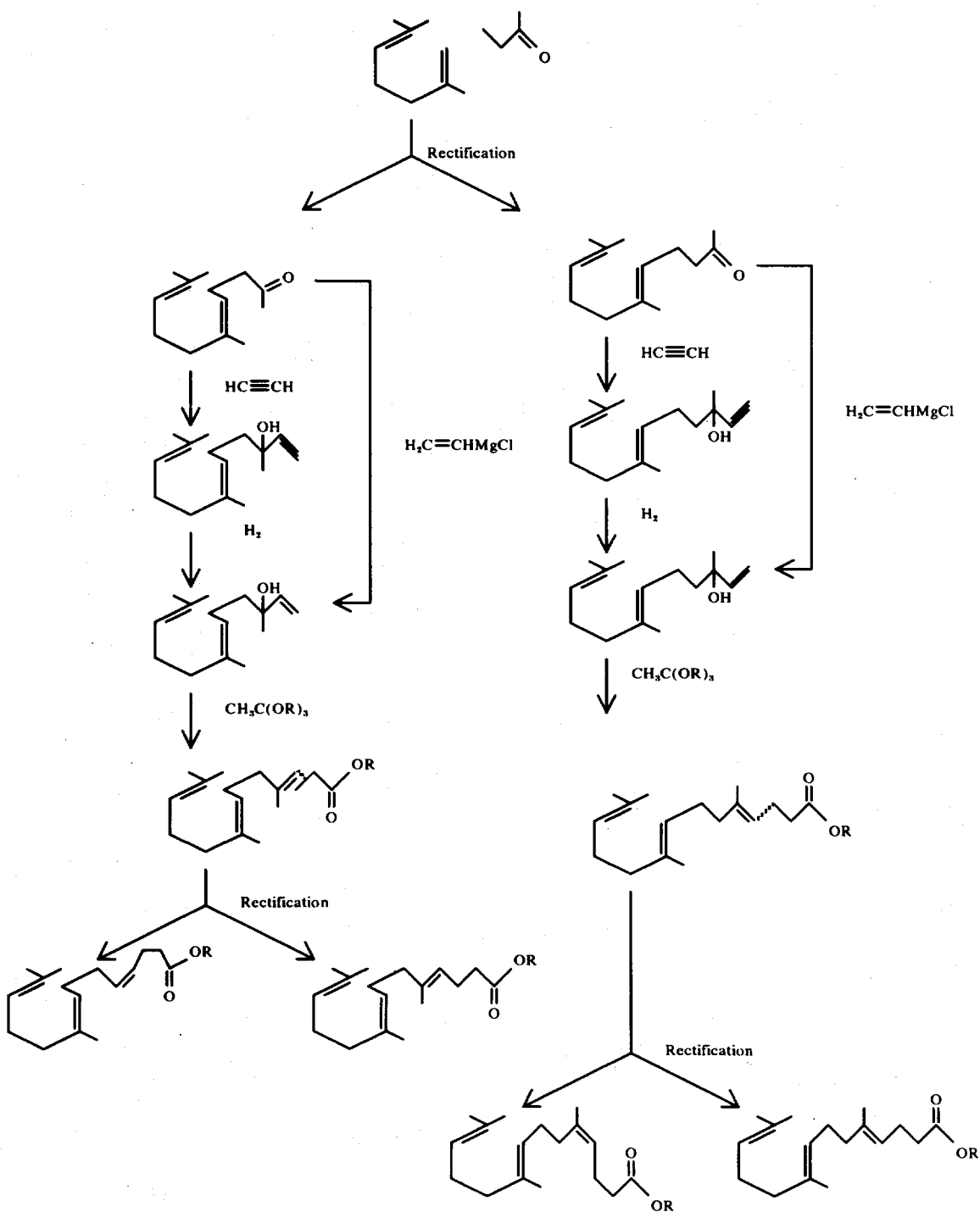

More specifically, the above process is a process wherein a mixture of cis- and trans-geranylacetones is separated by rectification, the geranylacetone is converted to cis- or trans-nerolidol and the so obtained nerolidol is reacted with an orthoacetic acid ester. It is a great advantage of the present process that a small number of steps is involved therein and a total yield thereof is remarkably high.

Next, each step of this invention will be illustrated in detail as following.

1. On preparation of $\Delta^5$-cis- and $\Delta^5$-trans-geranylacetone Geranylacetone has the following formula:

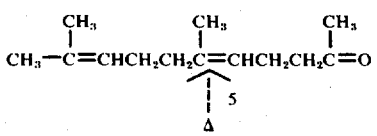

The stereospecific geranylacetone as such is not only used in perfumes, but also very important for preparation of nerolidol and farnesol which are used in perfumes of high grade as well as 3,7,11-trimethyl-2,6,10-dodecatrienoic acid ester having juvenile hormone activity and farnesylacetic acid ester having anti-ulcer activity.

As isolation methods of a mixture of cis- and trans-geranylacetone, there have been known a semicarbazone-recrystallization method reported by O. Isler et al. in Helv. Chim. Acta., 39, 897 – 904 (1956) and a recrystallization method at lower temperature reported by O. Isler et al. in Helv. Chim. Acta., 43, 1745 – 1751 (1960), but these methods are impractical in industry because of use of several reagents and complicated operations.

On the other hand, an isolation method by distillation for separation of cis- and trans-isomer, as reported by R. B. Bates et al. in J. Org. Chem., 28, 1086 – 1089 (1963) is suitable for separation of a mixture of nerol and geranylacetone having 10 carbon atoms but supposed to be very ineffective for that of farnesol of higher molecular weight having 15 carbon atoms.

But the present inventors have found that on rectification of geranylacetone having 13 carbon atoms, the separation of cis- and trans-isomer is very effective and the isomerization cis-isomer ⇌ trans-isomer proceeds catalytically at the same time, and completed this invention.

According to this invention, it is possible to perform the separation of a desired compound in almost quantitative yield in a simple operation without limit to any ratio of cis- and trans-isomer in the starting material.

Also, on preparation of cis-geranylacetone, as the cis-isomer has lower boiling point than that of the trans-isomer, it is not always necessary to carry it out batchwise and it can be carried out under continuous system by taking out preferably the cis-isomer simultaneously with the reaction in the presence of isomerization catalyst.

As to theoretical plate numbers of a rectifying column for the practice of this invention, it is theoretically possible to separate using a rectifying column having lower theoretical plate numbers, but it is necessary to use at least more than 10 practical plates in the case of obtaining a cis- or a trans-isomer in high purity in a single distillation. Because of the high boiling point of geranylacetone used for separation in this invention, the distillation must be carried out under reduced pressure. For obtaining the desired compound in high yield, the use of a rectifying column having higher theoretical plate numbers is preferred, but the use of such a column causes an increase in pressure-loss during distillation. On distillation under reduced pressure, the high pressure-loss causes the stability of distillation to worsen, the temperature of liquid in the still to increase and the stability of the material to decrease so that the plate numbers cannot be increased without limit. From these points of view, as the rectifying column used for this invention, a column having about 10 – 100 of practical plates is preferred and on consideration of economy, a column having about 20 – 60 plates is more preferred. As to structure of a column, a column having a small pressure-loss per plate is preferred.

The reflux ratio varies with the structure of the column but is 2 – 100, preferably about 5 – 30. The distillation of this invention can be effected in a batchwise, continuous or semibatchwise manner; the manner chosen is determined by economical considerations including amount of production.

The isomerization reaction is a reversible reaction and the ratio at equilibrium of cis- and trans-isomers depends on temperature; the ratio is, for example, about 4 : 6 at 170° – 200° C and about 35 : 65 at 130° – 140° C.

As catalysts used for the isomerization reaction, there can be mentioned transition metal catalysts of VI, VII or VIII group such as tungsten, iron, nickel, cobalt, ruthenium, rhenium, platinium, osmium and iridium, and organic sulfur compounds. The tungsten and ruthenium catalysts are practically used in the forms of the following several derivatives: halides, sulfide compounds, chalcogenites, chalcohalides, nitrosochlorides, nitrosylhalides, and salts of inorganic oxonic acids such as sulfates, nitrates, carbonates, arsonates, arsenates, germanium salts, perchlorates, sulfites, nitrites, and salts of aliphatic, alicyclic or aromatic acids or alcohols or phenols such as acetic acid, propionic acid, oxalic acid, naphthenic acid and sulfonic acid.

As complex catalysts, there can be mentioned chelate compounds of acetylacetonato, benzoylacetonato, glyoximato, quinolato and salicylaldehydato ligands, compounds coordinated with carbon monoxide, monoolefin, diolefin, polyolefin and cyclopentadienyl radicals.

The compounds coordinated with nitorgen compounds, phosphine compounds, arsine, stibine and nitriles may also be used.

Of course, these compounds can be made insoluble by coordinating these compounds with formation of carbon-phosphorous bonding on high molecular compounds such as polyvinylpyridine containing nitrogen and polystyrene compounds so that the recovery process of catalysts can be made easily. These catalysts can be used on active alumina, silica, pumice, fuller's earth and diatomaceous earth.

Among tungsten and ruthenium catalysts, the catalysts having high activities and high selectivities are as follows: tungsten disulfide, complex catalysts such as acetylacetonatoruthenium, glyoximatoruthenium and salicylaldehydatoruthenium and salts such as ruthenium salicylate and ruthenium propionate.

As organic sulfur compounds used for isomerization catalysts, there can be mentioned, for example, phenyldisulfide, alkyldisulfide, phenylmercaptan, thiocresol, alkylmercaptan and thiocarboxylic acid.

The reaction can be performed under air atmosphere but is prefered to be performed under an inert gas atmosphere in order to elevate the selectivity.

The reaction can be carried out at temperatures of 50° – 300° C but preferably at a range of 120° – 210° C.

An amount of catalyst used must be determined dependent on kinds of catalyst, reaction temperature, economical points and selectively of the reaction and cannot be generally specific; however it is 0.001 – 20 weight% to geranylacetone. On the reaction at 150° – 210° C using ruthenium and tungsten compounds, it is preferred to be 0.01 – 10 weight%, and on the reaction at 120° – 160° C using organic sulfur compounds, it is preferred to be 0.1 – 10 weight%.

In the case of using organic sulfur compounds as catalysts, it is possible to isomerize radically be adding 0.01 – 20% of radical initiator such as azobisisobutyronitrile (AIBN) and benzoyl peroxide (BPO) to the said organic sulfur compounds but the isomerization can be well performed with the single use of organic sulfur compounds.

The use of a reaction solvent is not necessary but hydrocarbons such as squalane which are stable and inert to the reaction under the said reaction conditions may be used.

The reaction always need to be continued until the equilibrium composition is obtained and can be stopped on the way. And in case where the desired compound is a cis-isomer, it is possible to obtain the desired compound in almost quantitative yield by distillation of the mixture under isomerization reaction and by shifting the equilibrium to the formation system.

After the reaction, in case the catalyst is not removed, the reverse-isomerization is apt to occur in case where the reaction mixture is heated for a long time for rectification so as to separate a trans-isomer at the next step. Therefore, the reaction mixture is subjected to single distillation as separation process of catalyst and while the distillate is subjected to rectification, the residue containing the catalyst is preferred to be reused for isomerization reaction. Of course, it is possible to inactivate the catalyst chemically or adsorb it physically or separate it by steam distillation.

2. On preparation of $\Delta^6$-cis- and $\Delta^6$-trans-nerolidol
nerolidol has the following formula:

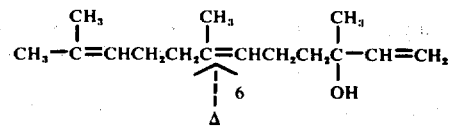

The stereospecific nerolidol as such has a weak but sweet flower odor and is of high grade as a perfume which is used for preparation of flower essence oils such as jasmine and violet and very important for preparation of an intermediate of farnesol, 3,7,11-trimethyl-2,6,10-dodecatrienoic acid ester having juvenile hormone activity and farnesylacetic acid ester having anti-ulcer activity.

Nerolidol has been prepared industrially as an intermediate for preparation of isophytol which is used as a starting material for preparation of Vitamin E. Its representative synthetic route is illustrated as follows:

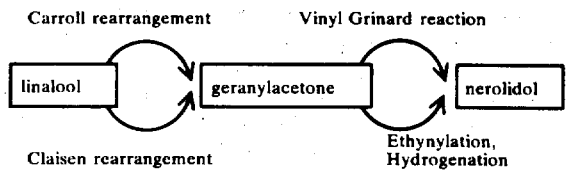

That is, it can be prepared by the following: a process for preparation of nerolidol in high yield which comprises reacting linalool with an equimolar amount of diketene or ethyl acetoacetate, subjecting the resultant to Carroll rearrangement under heating and decarboxylating or subjecting the resultant to Claisen rearrangement by heating it with isopropenyl ether in the presence of an acidic catalyst such as p-toluene-sulfonic acid to obtain geranylacetone and reacting it with a Grignard reagent or ethynylating it and partially hydrogenating the resultant product. But the nerolidol obtained by this method is a mixture of about 4 : 6 ratio for cis- to trans-isomer.

On the other hand, there has been known a process for preparing stereospecific nerolidol which comprises halogenating $\Delta^2$-cis-3,7-dimethyl-2,6-octadien-1-ol or $\Delta^2$-trans-3,7-dimethyl-2,6-octadien-1-ol as starting materials with, for example, phosphorous tribromide under preservation of stereostructure, condensing the resultant product with ethyl acetoacetate in the presence of an alkali and then hydrolyzing and decarboxylating the resultant product to obtain cis- or trans-geranylacetone and reacting the acid compound with vinyl Grignard or ethynylating and partially hydrogenating the said compound. But this process has numerous steps and needs a troublesome procedure for preserving the stereostructure so that it is not suitable for industrial preparation of said compound in large scale. But, we have found a separation method of $\Delta^5$-cis- and $\Delta^5$-trans-geranylacetone, as already described above. The $\Delta^5$-cis- and $\Delta^5$-trans-geranylacetone prepared based on these findings give a stereospecific nerodidol, that is, respectively $\Delta^6$-cis- and $\Delta^6$-trans-nerolidol when they are reacted with a vinyl Grignard reagent or ethylated and partially hydrogenated.

In carrying out the process of this invention, the ethynylation of cis- or trans-geranylacetone can be easily effected in liquid ammonia in the presence of a catalyst, e.g., metallic sodium, metallic potassium, sodium alkoxide, potassium alkoxide, sodium hydroxide, potassium hydroxide et al. The method disclosed in U.S. Pat. No. 3,082,260 may be applied to carry out the ethynylation of the present invention. Partial hydrogenation may be effected, for example, by the use of Lindlar catalyst in a lower hydrocarbon, e.g., n-hexane.

Alternative methods according to vinyl Grignard reaction may be conducted by conventional procedures, for example, in such a solvent as tetrahydrofuran or diethyl ether as reported by A. Ofner et al. in Helv. Chim. Acta., 42, 2577 (1959). On the other hand, a mixture of cis- and trans-geranylacetone can be used as a starting material for the preparation of a stereospecific nerolidol.

The separation of cis- and trans-isomers by distillation, as reported by R. B. Bates et al. in J. Org. Chem., 28, 1086 – 1089 (1963) is suitable for a mixture of nerol and geraniol having 10 carbon atoms but it is very ineffective for separation of farnesol having a larger molecular weight with 15 carbon atoms.

But we have found that the better separation of cis- and trans-isomer of nerolidol can be effected unexpectedly as a result of rectification of nerolidol having 15 carbon atoms. And the isomerization reaction of cis-isomer ⇌ trans-isomer proceeds catalytically.

According to the process of this invention, it is possible to prepare the desired cis- or trans-isomer in a simple operation in almost quantitative yield without limit to any ratio of cis- and trans-isomer in the starting material.

Also, on preparation of cis-nerolidol, as the cis-isomer has a lower boiling point than that of the trans-isomer, it it always unnecessary to carry out it batchwise; preferably, it can be carried out in a continuous system by taking out the cis-isomer simultaneously with the reaction in the presence of the isomerization catalyst.

As to theoretical plate numbers of a rectifying column for the practice of this invention, it is theoretically possible to separate using a rectifying column having lower theoretical plate numbers but it is necessary to use at least more than 10 practical plates in the case of obtaining a cis- or trans-isomer in high purity in a single distillation. Because of the fact that nerolidol used for separation of this invention has very high boiling point and is subject to dehydration by heating, the vacuum distillation must be adopted for distillation. For obtaining the desired compound in high yield, the case of a rectifying column having higher theoretical plate numbers is preferred, but an increase in use of such a column causes the pressure-loss during distillation. On distillation under reduced pressure, the high pressure-loss causes the stability of distillation to worsen, the temperature of liquid in the still to increase, and the stability of the material to decrease so that the plate numbers cannot be increased without limit. From these points of view, as a rectifying column used for this invention, a column having about 10 – 100 of practical plates is preferred and on consideration of economy, a column having about 20 – 60 plates is more preferred. As to structure of a column, a column having a small pressure-loss per plate is preferred.

The reflux ratio varies with the structure of column but is 2 – 200, preferably about 5 – 30. The distillation of this invention can be effected in a batchwise, continuation or semi-batchwise manner; the manner chosen is determined by economical considerations including amount of production.

The isomerization reaction is a reversible reaction and the ratio at equilibrium of cis- and trans-isomers depends on temperature and the ratio is, for example, about 4 : 6 at 170° – 200° C and about 35 : 65 at 130° – 140° C.

The catalysts used for isomerizing nerolidol are the same as those used for isomerizing geranylacetone, as already described above. The reaction conditions of this isomerization are the same as those for isomerization of geranylacetone.

3. On preparation of a stereospecific farnesylacetic acid or its esters

The $\Delta^6$-trans- and $\Delta^6$-cis-nerolidol give, respectively, a mixture of $\Delta^4$-cis-$\Delta^8$-trans- and $\Delta^{4,8}$-trans-farnesylacetic acid esters and a mixture of $\Delta^4$-trans-$\Delta^8$-cis- and $\Delta^{4,8}$-cis-farnesylacetic acid esters when they are reacted with orthoacetic acid or its esters. The above reactions are illustrated below:

nol, o-, m- or p-cresol, o-, m- or p-nitrophenol or hydroquinone.

Reaction temperature may be practicably between 50° C. and 200° C., preferably between 130° C. and 180° C.

The orthoacetic acid ester is theoretically employed in an equimolar amount with respect to nerolidol, but an excess amount thereof may be employed for both reagent and solvent. However, it is preferable in view of a recovery step to employ the ester in a 1 – 4 times molar amount to the amount of nerolidol.

Catalyst concentration may be practicably of 0.1 – 20% by weight to the starting alcohol, but 1 – 10% by weight is preferred in view of reaction rate and selectivity. Lower alcohols are formed in situ as by products with transesterification as the reaction proceeds and they should be withdrawn out of the reaction system. After completion of the reaction, the reaction mixture may be subjected to vacuum distillation with or without preliminary treatment such as extraction or washing with water.

Usually, the present rearrangement can proceed nearly quantitatively with a conversion of nerolidol of not less than 95% and a selectivity to farnesylacetic acid ester of not less than 98%. This clearly demonstrates advantages of this invention in an extremely high yield and a single step, as compared with the previously known method, for example, that disclosed in helv. Chim. Acta., 53, 1827 (1970). A proportion of cis-form to trans-form in the double bond shifted through rearrangement is about 35 : 65.

The compounds obtained by the aforesaid process having the formula (2), are preferable for separation of a mixture of $\Delta^{4,8}$-cis-form and $\Delta^{4,8}$-trans-$\Delta^8$-cis-form or of $\Delta^4$-cis-$\Delta^8$-trans form and $\Delta^{4,8}$-trans-form into each form by rectification. In case of an alkyl or alkenyl group of more than 6 carbon atoms, practical separation is not feasible due to cosiderably higher boiling point together with lower separation efficiency. More preferable are those compounds wherein an alkyl or

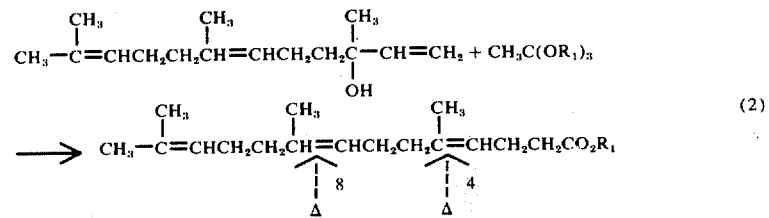

(2)

wherein $R_1$ represents a lower alkyl having 1 – 6 carbon atoms, cycloalkyl having 3 – 6 carbon atoms, lower alkenyl having 2 – 6 carbon atoms and cycloalkenyl radical having 3 – 6 carbon atoms. As lower alkyl radicals having 1 – 6 carbon atoms of $R_1$, there can be mentioned methyl, ethyl, propyl, isopropyl, n-butyl, isobutyl, n-pentyl, isopentyl, n-hexyl and isohexyl radicals et al., as cycloalkyl having 3 – 6 carbon atoms, cyclobutyl, cyclopentyl, and cyclohexyl, as lower alkenyl radical having 2 – 6 carbon atoms, vinyl, propenyl, butenyl, pentenyl and hexenyl radicals in which the double bond may be at any position, and as cycloalkenyl radical having 3 – 6 carbon atoms, cyclopentenyl, and cyclohexenyl.

The above reaction may be effected by heating in the presence of an acidic catalyst such as aliphatic acid, e.g., acetic acid, propionic acid, butyric acid, isobutyric acid, oxalic acid or adipic acid or a phenol, e.g., phealkenyl group has not more than 4 carbon atoms.

Furthermore, we have found that a mixture of farnesylacetic acid esters having 4 isomers gave pure $\Delta^{4,8}$-trans-farnesylacetic acid ester by fractional distillation using a rectifying column with high efficient separation capacity as a result of the extensive inventigations with a mixture of farnesylacetic acid esters having the formuls (2), wherein $R_1$ represents only the above lower alkyl or lower alkenyl radicals.

Preferred numbers of the theoretical plates installed in a rectifying column employed in the present process of this invention may vary dependent upon kinds of esters used. Ordinarily, it is preferred to use a rectifying column having many plates which can give excellent separation. Although it is possible in principle to separate one of these products even through a rectifying column with a small number of theoretical plates, at least more than 10 practical plates is necesary to obtain the desired $\Delta^{4,8}$-trans-isomer in high purity by one distillatory operation.

The distillation must be carried out under reduced pressure, because the derivatives of farnesylacetic acid have very high boiling points. It is preferable to use a rectifying column with a large number of theoretical plates. But, on the other hand, such a column results in substantial loss of pressure in the column. The number of plates should not be increased without limit, because the incresed pressure loss in the column under reduced pressure is disadvantageous in that the stability of distillation is lowered and the product becomes unstable in the still due to the increased temperature.

With respect to the rectifying column employed in this invention, it is preferred to use a column with 10 – 100 practical plates, more preferably a column with 20 – 60 practical plates, taking the economical efficiency into consideration. It is needless to say that a column with a structure which gives little pressure loss per one plate is preferable. Reflux ratio is dependent upon the kind of the column employed. The distillation is preferably carried out a reflux ratio of 2 – 100, more preferably of 5 – 30. By carrying out the distillation with a bottom temperature below 280° C., $\Delta^{4,8}$-trans-isomer is obtained in a particularly high yield. The distillation in this invention can be carried out by batch system, continuous system or semi-batch system. Whether one or the other is the best varies dependent upon economic factors such as output, etc. For example, 533 g of a mixture of ethyl farnesylacetate isomers, which was composed of 15% of $\Delta^{4,8}$-cis-isomer, 24% of $\Delta^{4}$-trans-$\Delta^{8}$-cis-isomer, 23% of $\Delta^{4}$-cis-$\Delta^{8}$-trans-isomer and 38% of $\Delta^{4,8}$-trans-isomer, was fractionated through a rectifying column with 40 theoretical plates with a bottom temperature of 175° C and a reflux ratio of 10 – 20 to give 150.0 g of $\Delta^{4,8}$-trans-isomer. The isomer was recovered in a high yield of 74% from $\Delta^{4,8}$-trans-isomer in the starting mixture. The separation of $\Delta^{4,8}$-cis-isomer was possible. But, with respect to $\Delta^{4}$-cis-$\Delta^{8}$-trans-isomer and $\Delta^{4}$-trans-$\Delta^{8}$-cis-isomer, it was almost impossible to separate them respectively in pure form.

In carrying out the separation of the stereo-isomers of farnesylacetic acid or its esters by rectification, it is preferred that R in the formula (1) is a hydrogen atom or such a radical as an alkyl, cycloalkyl, alkenyl or cycloalkenyl radical having not more than 6 carbon atoms. In case where R is such a radical as an alkyl or alkenyl having more than 6 carbon atoms, the separation by distillation is difficult in practice, because the efficiency is decreased as the boiling point of compound is increased. It is more preferable that R is such a radical as alkyl or alkenyl having not more than 4 carbon atoms. There may be employed many preparative methods (a) – (d) to synthesize the starting material mixture of $\Delta^{4}$-cis, trans- and $\Delta^{8}$-trans, cis-isomers of farnesylacetic acid esters, which are already described above. In manufacturing a large amount of the product industrially, method (d) is the most preferably one. When nerolidol is heated to 100°–200° C with orthoacetate in the presence of an acidic catalyst, the alcohol is liberted as the transesterification and Claisen-rearrangement are effected. By removing the alcohol from the reaction system, the desired product is obtained in high yield of more than 95% of the conversion based on the amount of nerolidol and more tha 98% of selectively to farnesylacetate. The reaction mixture is directly distilled to give farnesylacetate in more tha 90% based on the starting nerolidol. By further fractionating the distillate mentioned above, $\Delta^{4,8}$-trans-farnesylacetate is separated selectively. When necessary, it may be subjected further to transesterification.

The above rectification can be effected under isomerization.

The isomerization in this invention means a reaction which changes only the configuration at a double bond from cis-form to trans-form and vice versa with no migration of a double bond. Many of the isomerization procedures have been investigated. They are to be classified roughly into three groups:

A. A method, in which isomerization is carried out by producing a double bond again after chemical treatment of a double bond to be isomerized.

B. A method in which a photochemical reaction is applied.

C. A method in which a catalyst is employed.

To explain more concretely in regard to method (A), an addition reaction to a double bond to be isomerized, such as epoxidation, halogenation, halohydrination, thioetheration or sulfonation, is carried out and subsequently an elimination reaction is conducted to form a mixture of isomers having cis and trans configuration at a doble bond. This procedure, as reported by J. W. Cornforth et al. in J. Chem. Soc., 1959, 112 – 127 and ibid., 1959, 2539 – 2547, has been applied as a method for stereospecific synthesis of squalene. However, this method is complicated in its procedure and not satisfactory in the yield of desired compound. The method (B), in which photochemical reaction is conducted, can effectively change the ratio of cis and trans-isomers merely by ultraviolet radiation at a low temperature. In this reaction, of course, its selectivity can be increased by using a photosensitizer or a solvent. However, in order to obtain the isomerized product with high selectivity, the reaction should be carried out in a solution of low concentration, the amount of which is about 1 – 10%.

The isomerization by a catalyst, method (C), is the most preferably one to manufacture a large amount of product industrially. A catalyst with high selectivity is naturally required to obtain such a compound suitable as pharmaceuticals as farnesylacetic acid or its esters which carries many double bonds and functional groups thereon.

The reaction can be carried out in a homogeneous system at from room temperature to 150° C in the presence of an acidic catalyst such as phosphoric acid, hydrochloric acid, p-toluenesulfonic acid, zinc chloride or boron trifluoride, etc. It can also be carried out at 100° – 200°C in the presence of a basic catalyst such as alkali metal alcoholate, sodium hydroxide, or potassium hydroxide etc. Both of the vapor-phase and liquid-phase reactions can be applied by using a catalyst such as silica-alumina or chromium oxide. However, these reactions are accompanied by such a side-reaction as migration of a double bond and production of higher-boiling substances. Therefore, these reactions have an effect when considering the said high selectivity. In addition to the catalyst as mentioned above, catalysts composed of tungsten which belongs to group VI, catalysts composed of iodacetates which belong to group VII or catalysts composed of iron, osmium or illidium which belongs to group VIII answer to the purpose of this invention.

More concretely speaking, transition metals which belong to groups VI, VII or VIII, such as tungsten, iron, nickel, cobalt ruthenium, rhenium, palladium, platinium, osmium and iridium, etc., are appropriately used as catalysts in a form of several kinds of their derivatives. That is, they are employed in a form of halogenated compounds, sulfides, chalocohalides, nitrosochlorides, nitrosylhalides, salts of inorganic oxoacids such as sulfates, nitrates, phosphates, carbonates, arsonates, arsenates, germanates, perchlorates, sulfates or nitrites, salts of such organic acids as propionic acid, oxalic acid, or naphthenic acid, alcoholates or phenolates. And they are also used in a form of a chelate such as acetylacetonato, benzoylacetonato, glyoximato, quinolato or salicylaldehydato. As a ligand, carbon monoxide, monoolefin, diolefin, polyolefin or cyclopentadiene may be coordinated. Nitrogen compounds, phosphine compounds, arsines, stibines or nitriles are appropriately coordinated as a ligand. The recovery of the catalysts used can be easily carried out by coordinating these catalysts to a nitrogen-containing high polymer such as polyvinylpyridine, or styrene and by forming carbon-phosphorus bonds to insolubilize them. Naturally, these catalysts can be carried on active alumina, silica, pumice, fuller's earth or kieselgulir. Although almost of these catalysts were used as catalysts for the isomerization of allylic alcohols or the dimerization of alkynols as disclosed in British Patent No. 1,256,184; U.S. Pat. application Ser. No. 571,004; or Japanese Patent Application No. 61204/74, (and corresponding U.S. Ser. No. 487,043 now U.S. Pat. No. 3,928,403) we have found that these catalysts might be applicable to steric isomerization reaction between cis-form and trans-form of farnesylacetic acids, esters thereof, geranylacetones and nerolidols. It has been clarified that the ruthenium catalyst shows particularly high activity and selectivity. It is capable of being employed industrially, taking its cost and stability into consideration. Almost all the well-known isomerization reactions using a ruthenium catalyst intended for the migration of double bond can be used. Therefore, it has been considered that its application to this invention is difficult. However, according to our investigation, it is possible to change, by selecting the condition of the amount of catalyst and the reaction temperature, only the stereo-chemical structure from cis to trans or from trans to cis with little migration of a double bond. Among the ruthenium compounds, the chelate compounds, such as acetylacetonato, glyoxymate, quinolato or salicylaldehydato chelate, are most suitable to practice of the present invention. For example, 100 g of ethyl $\Delta^{4,8}$-cis-farnesylacetate added with 0.1 g of acetylacetonatoruthenium was heated at 100° C in an inert atmosphere for 2 hours to give a substance in 45% of conversion and 99.5% of selectivity, which was composed of 55% of $\Delta^{4,8}$-cis-isomer, 25% of $\Delta^4$-cis-$\Delta^8$-trans-isomer and $\Delta^4$-trans-$\Delta^8$-cis-isomer, and 20% of $\Delta^{4,8}$-trans-isomer. The conversion ratio may be increased up to about 84% by continuing the reactions.

The reaction is an equilibrium one. Therefore, a thermoequilibrated composition of 16 : 48 : 36 of the aforesaid ratio is obtained, starting from any one of $\Delta^{4,8}$-cis-isomer, $\Delta^4$-cis-$\Delta^8$-trans-isomer, $\Delta^4$-trans-$\Delta^8$-cis-isomer or $\Delta^{4,8}$-trans-isomer. The ratio of the component produced is of course dependent upon the reaction temperature.

For example, the ratio of $\Delta^{4,8}$-trans-isomer produced is increased up to about 38% at 150° C and it is decreased to 34% at 230° C. The optimum conditions of the reaction temperature, the catalyst concentration, the reaction velocity and the amount of catalyst in industrial manufacturing should be selected. Practically, the time of the reaction need not be so long as to equilibrate the reaction. The conversion may be suppressed at about 20 - 30%. As for the amount of the catalyst, if explained by exemplifying acetylacetonatoruthenium, within 0.001 - 20% by weight of the catalyst based on farnesylacetic acid or its esters is employed, and the reaction temperature is within 50° - 300° C. The reaction may be carried out in an atmosphere of air. More preferred, the reaction is conducted in an inert atmosphere at a temperature of about 150° - 200° C in the presence of 0.01 - 1.0% by weight of catalyst. Although the reaction can be carried out without the use of a solvent, it may also be carried out with the use of a solvent which is stable and inert under the abovementioned reaction condition, e.g., a hydrocarbon such as squalane. When such a catalyst as ruthenium catalyst, which is difficult to be removed, is not separated off after the isomerization reaction, there is the possibility of the reverse isomerization reaction by heating for a long time in such a operation as rectification. It is preferred that the residue, which contain the catalyst, is recycled to carry out isomerization again after simple distillation to remove the catalyst and the distillate is further rectified.

Of course, chemical deactivation and physical absorption of the catalyst can be carried out to avoide the reserse isomerization reaction. With the use of the catalyst-system, which is composed of organosulfur compounds and radical initiators, the isomerization reaction also proved to progress selectively as well as with the aforementioned ruthenium catalyst. The isomerization reaction, which is conducted at a temperature of about 50° - 200° C in the presence of about 0.1 - 30 mole %, based on farnesylacetic acid or its ester, of sulfur compound such as phenyldisulfide, alkyldisulfide, phenylmercaptan, thiophenol, thiocresol and thiocarboxylic acid, and about 0.01 - 20% by weight of radical initiator (e.g., azobisisobutyronitrile AIBN, benzoylperoxide BPO) based on the sulfur compound, gives a thermoequilibrated mixture with high selectivity.

This catalyst is superior to the ruthenium catalyst in that the reverse isomerization reaction is avoidable in rectification because the sulfur compound can be removed by distillation.

4. Hydrolysis and transesterification of the stereospecific farnesylacetic acid esters To obtain the stereospecific farnesylacetic acid and its esters having the formula (1) from the stereospecific farnesylacetic acid esters having the formula (2), various methods such as the methods described in U.S. Pat. No. 3,154,570 may be used. Particularly among these methods, hydrolysis or/and esterification or transesterification may be used. As already described above, the separation of farnesylacetic acid esters having more than 6 carbon atoms by rectification is difficult in practice. In cases where R is a radical having larger numbers of carbon atoms, e.g., a geranyl or farnesyl radical, etc., the compound shows an excellent anti-ulcer activity as reported by E. Adami et al. in Med. Exptl., 7, 171 - 176 (1962). As reported by G. Pala et al., however, it is practically impossible to separate their isomers by distillation. In the preparation of these compounds, the most preferable method is to hydrolyze or/and esterify or transesterify the above fractionated compound having the formula (2) to obtain the compound having the formula (1). In the formula (1), R represents hydrogen atom, an alkyl, alkenyl, alkynyl, cycloalkyl, cycloalkenyl, aryl, aralkyl, aralkenyl or heterocyclic radical having not more than 20 carbon atoms. For example, ethyl; allyl; geranyl; farnesyl; cyclobutyl; cyclopentyl; cyclohexyl; cyclopentenyl; cyclohexenyl; propargyl; phenyl or naphthyl which may be substituted with lower alkyl having 1 - 4 carbon atoms, halogen atoms, alkoxy radical having 1 - 4 carbon atoms or nitro radical; furfryl; phytyl; carvacryl; or cinnanyl radical.

The above hydrolysis or/and esterification or transesterification can be performed by a usual method in the art. Particularly, it is suitable to apply the methods disclosed in the specification of U.S. Patent No. 3,154,570 at column 2, line 30 to column 3, line 56, or the Japanese Patent Published No. 31088/73 (48-31088), to the exchange of an alcoholic residue $R_1$ of the formula (2) to an alcoholic residue R of the formula (1).

The farnesylacetic acid obtained by the hydrolysis of a mixture of the isomers or by the other methods can also be subjected to rectification to give the stereospecific farnesylacetic acid. But this rectification is not so well performed as recification of the farnesylacetic acid esters having the formula (2) because of its high boiling point and instability to heating.

This invention is illustrated in detail by the following examples, but these are not meant to limit the scope of the invention.

EXAMPLE 1

After 6.016 g (purity: 95%) of linalool and 3,444 g of diketene were reacted in the presence of 163 g of triethylamine, 240 g of aluminium isopropoxide was added and the mixture was subjected to Carroll rearrangement by heating. Vacuum distillation of the reaction mixture gave 5,200 g of a mixture of cis- and trans-geranylacetone in a ratio of 4 : 6 having b.p. 68° − 74° C (0.4 mmHg).

This material was subjected to reactification using a rectifying column having about 40 theoretical plates in a reflux ratio of 10 − 20 to give 830 g of cis-geranylacetone having b.p. 74° − 76° C (0.4 mmHg) (distillation yield: 40% of the cis-isomer charged) and 2,420 g of trans-geranylacetone having b.p. 77° − 79° C (0.4 mmHg) (distillation yield: 78% of the trans-isomer charged) and 1,950 g of other intermediate distillate.

Figure 2:
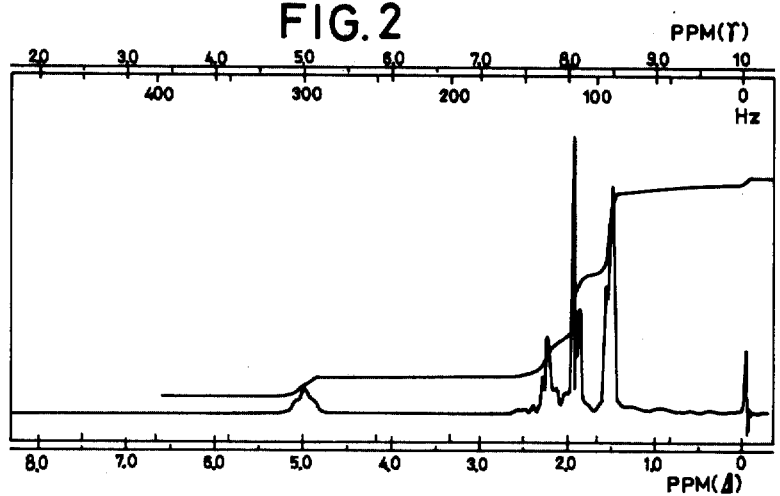

The refractive index of the said cis-geranylacetone showed $n_D30 = 1.4628$ and its NMR spectrum in carbon tetrachloride is shown in FIG. 1. The refractive index of the said trans-geranylacetone showed $n_D^{30} = 1.4634$ and its NMR spectrum in carbon tetrachloride is shown in FIG. 2.

Next, 830 g of the cis-isomer obtained as fore-running and 1,950 g of the intermediate distillate were mixed and reacted at 140°C for 8 hours in the presence of 140 g of p-thiocresol in an atmosphere of nitrogen. The analysis of the reaction mixture by gas chromatography showed that the ration of cis- and trans-isomer was about 45 : 55. Further rectification of the reaction mixture using a rectifying column having about 40 theoretical plates gave 1,844 g as fore-running containing p-thiocresol of catalyst and the cis-isomer as main components and 1,070 g of trans-isomer.

Further, after 1,844 g of the fore-running was reacted at 140°C for 12 hours in an atmosphere of nitrogen, the gas chromatographic analysis of the reaction mixture showed that the ratio of cis- and trans-isomer was 42 : 58.

EXAMPLE 2

In a flask provided with a rectifying column having about 40 theoretical plates were placed 1,000 g of a mixture of cis- and trans-geranylacetone in a ratio of about 4 : 6 and 2.0 g of acetylacetonatoruthenium (III) and the mixture was rectified at 175° − 179° C of the column bottom temperature and at 130°− 135° C of the top column temperature at a reduced pressure of 5 − 7 mmHg under reflux ratio 10 to give 968 g of the distillate, the purity of the cis-isomer of whih was 99.4% as a result of gas chromatography.

EXAMPLES 3 − 9

A mixture of cis- and trans-geranylacetone in a ratio of 4 : 6 was subjected to rectification in the same manner as in example 1 and the fore-running obtained in taking out the trans-isomer was isomerized in the presence of several kinds of isomerization catalysts. The reaction mixture was roughly distilled at 120°− 130° C of the column bottom temperature and the distillate was again rectified to give the trans-isomer. The results were tabulated in Table 1. In examples 4 and 7, the catalyst was distilled out on rough-distillation, but separated as low-boiling distillate on rectification.

Table 1

| Example | Ratio of cis- : trans-isomer in starting material | Catalyst | Conditions of isomerization | | Ratio of cis-trans-isomer after isomerization | Yield* (%) |
|---|---|---|---|---|---|---|
| 3 | 72 : 28 | Ru (AA)₃ 0.2 wt. % | 180° C | 8 hrs. | 46 : 54 | 71 |
| 4 | 67 : 33 | 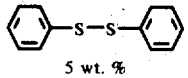 5 wt. % a small amount of BPO | 140° C | 18 hrs. | 42 : 58 | 73 |
| 5 | 70 : 30 |  5 wt. % | 140° C | 18 hrs. | 42 : 58 | 76 |
| 6 | 70 : 30 | Ru (AA)₃ 0.2 wt. % | 190° C | 5 hrs. | 47 : 53 | 73 |

Table 1-continued

| Example | Ratio of cis- : trans-isomer in starting material | Catalyst | Conditions of isomerization | | Ratio of cis-trans-isomer after isomerization | Yield* (%) |
|---|---|---|---|---|---|---|
| 7 | 70 : 30 | 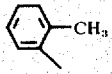  SH  5 wt. %  a small amount of AIBN | 140° C | 15 hrs. | 42 : 58 | 75 |
| 8 | 65 : 35 | $RuCl_2(PPh_3)_3$  0.5 wt. % | 170° C | 48 hrs. | 50 : 50 | 70 |
| 9 | 65 : 35 | $WS_2$  0.4 wt. % | 190° C | 8 hrs. | 47 : 53 | 64 |

*The yield is that of trans-isomer obtained after separation of the catalyst and rectification from the reaction mixture after isomerization.

EXAMPLE 10

After 1.5 g of acetylacetonatoruthenium was added to 500 g of cis-geranylacetone obtained by example 2, the mixture was heated at 190° C in an atomsphere of nitrogen. The reaction mixture was analyzed by gas chromatography. After 2 hours of the reaction, the conversion ration of cis-isomer was 32% and the selectivity of trans-isomer formed 97.4%.

After rough-distillation of the product, 472 g of a mixture of cis- and trans-geranylacetone was obtained, which was subjected to rectification to give 104 g of cis-isomer, 128 g of trans-isomer and 240 g of intermediate distillate.

EXAMPLE 11

1,360 g of the said mixture of geranylacetone (cis-/trans-≈ 4/6), which had been obtained in Example 1, was ethynylated in liquid ammonia in the presence of 176 g of metallic sodium and neutralized with ammonium chloride. The reaction mixture was extracted with ether and the extract was washed with water and dried. After the solvent was distilled off, the residue was subjected to vacuum distillation to afford 1,280 g of dehydronerolidol having b.p. 110° - 112° C (0.5 mmHg).

Further, 0.5 ml of quinoline and 20 g of 0.25% Pd-Lindlar catalyst was added in a solution of 1,280 g of the said dehydronerolidol in 2,000 ml of n-hexane and the mixture was hydrogenated at room temperature and normal pressure. After post-treatment, the reaction mixture was subjected to vacuum distillation to give 1,170 g of nerolidol having b.p. 105° - 110° C (0.5 mmHg).

Figure 4:
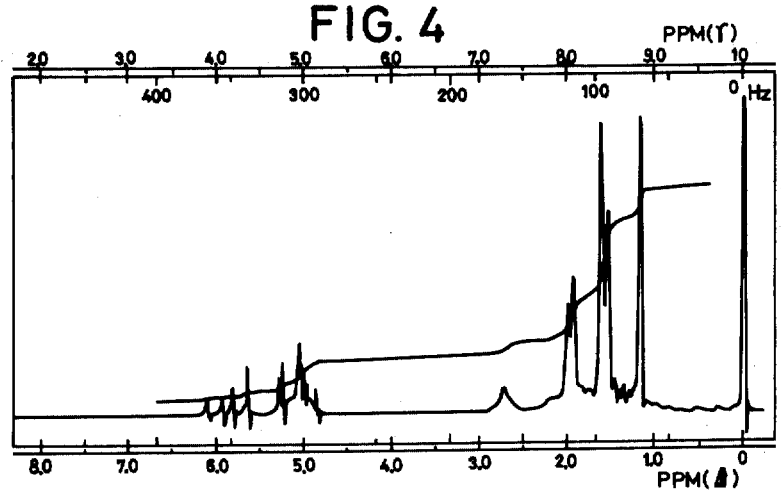

Next, 1000 g of a mixture of cis- and trans-nerolidol in a ratio of 40 : 60 was rectified using a rectifying column having about 40 theoretical plates at 135° - 140° C of the column bottom temperature at 0.3 - 0.5 mmHg of reduced pressure under reflux ratio of 10 to obtain 183 g of cis-nerolidol (0.3 mmHg). This yield was 46% of distillation yield for cis-isomer charged. Its refractive index was $n_D^{30} = 1.4753$ and its NMR spectrum in carbon tetrachloride is shown in FIG. 4. 324 g of trans-nerolidol was obtained from the distillate having b.p. 107° - 110° C (0.5 mmHg). This was 54% of distillation yield for trans-isomer charged. Its refractive index was $n_D^{30} = 1.4754$ and its NMR spectrum is shown in FIG. 6 477 g of intermediate distillate in a ratio of 46 : 54 of cis- : trans-isomer was also obtained.

Next, 183 g of cis-isomer obtained as fore-running and 477 g of the intermediate distillate were mixed to form a mixture of cis- and trans-isomer in a ratio of 61 : 39. After addition of p-thiocresol, this mixture was isomerized at 140° C for 4 hours under nitrogen atmosphere. The reaction liquid was analyzed by gas chromatography, which showed that the above ratio was 42 : 58.

Next, the reaction liquid was roughly distilled at below 130° C of column bottom temperature to give 632 g of the distillate. This distillate was rectified as described above using a packed rectifying column having about 40 theoretical plates to give 392 g of the fore-running in a ratio of 67 : 33 of cis- : trans-isomer and 227 g of trans-nerolidol as after-running.

EXAMPLE 12

Figure 3:
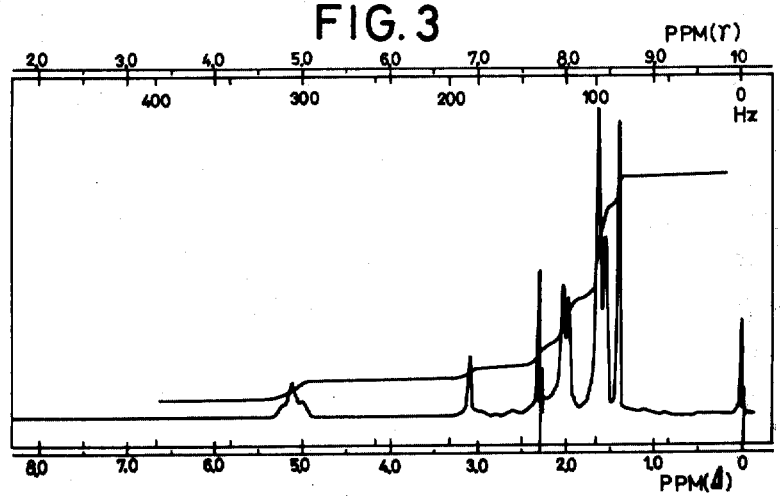

In a 2-l. three-necked flask 1 l. of liquid ammonia was placed and, after addition of 55.2 g of metallic sodium, acetylene gas was passed thereto and continued to pass until the reaction liquid turned from violet to white. 388 g of cis-geranylacetone was added to the ammonia mixture. While the liquid ammonia was under reflux, acetylene gas was bubbled thereto for 4 hours. After removing the ammonia, 110 g of ammonium chloride was added and neutralized. The reaction liquid was poured into water and extracted with ether. The extract was washed with water and dried over sodium sulfate and the solvent was distilled off. The residue was subjected to distillation under reduced pressure to afford 372 g of cis-dehydronerolidol having b.p. 133° - 135° C (5 mmHg) in a yield of 85%. Its refractive index was $n_D^{30} = 1.4750$ and its NMR spectrum in carbon tetrachloride is shown in FIG. 3.

Next, in a solution of 320 g of the said cis-dehydronerolidol in 1000 g of n-hexane, 0.15 ml of quinoline and 5.0 g of 0.25% Pd-Lindlar catalyst were added and the mixture was hydrogenated at room temperature under normal pressure. The reaction progress was analyzed with gas chromatography having PEG-20M (5%) at 150° C of the column temperature. When the cis-dehydronerolidol of the starting material disappeared, the reaction was supposed to be finished and the reaction mixture was filtered out with glass filter. After the filtrate was distilled, the residue was subjected to high vacuum distillation to give 314 g of cis-nerolidol having b.p. 99° - 102° C (0.3 mmHg). Its refractive index was $n_D^{30} = 1.4753$ and its NMR spectrum in carbon tetrachloride is shown in FIG. 4.

In the same manner, 1,360 g of trans-geranylacetone was ethynylated in the presence of 176 g of metallic sodium. After the reaction, 1,280 g of trans-dehydronerolidol having b.p. 112° C (0.5 mmHg) was obtained by vacuum distillation in a yield of 83%. Its refractive index was $n_d^{30} = 1.4771$ and its NMR spectrum in carbon tetrachlordie is shown in FIG. 5.

Next, in a solution of 1,000 g of trans-dehydronerolidol 0.5 ml of quinoline and 15 g of 0.25% Pd-Lindlar catalyst were added and the mixture was hydrogenated at room temperature under normal pressure. After after-treatment, the reaction mixture was subjected to high vacuum distillation to give 980 g of trans-nerolidol having b.p. 107° – 110° C (0.5 mmHg). Its refractive index was $n_d^{30} = 1.4754$ and its NMR spectrum in carbon tetrachloride is shown in FIG. 6.

EXAMPLE 13

According to the method reported by A. Ofner et al. in Helv. Chim. Acta., 42 2577 – 2584 (1959), cis- or trans-nerolidol was prepared respectively from cis- or trans-gernaylacetone. That is, in 420 ml of tetrahydrofuran was placed 12.5 g of freshly-prepared metallic magnesium turnings and 60 g of vinyl bromide was added dropwise thereto under water cooling to form a Grignard reagent. 50 g cis- or trans-gernaylacetone was added dropwise thereto at 25° C. The reaction mixture was neutralized with ammonium chloride and extracted with ether. The extract was dried over sodium sulfate and distilled off under reduced pressure. The residue was subjected to vacuum distillation to give cis-nerolidol from cis-geranylacetone in a yield of 82%. The product was identified by the standard product obtained in Example 12.

The trans-isomer was obtained in the same manner.

EXAMPLE 14

In a flask equipped with a rectifying column having about 40 theroretical plates 500 g of cis-nerolidol with 30 g of octadecamercaptan was placed and the mixture was subjected to vacuum distillation at 145° – 150° C column bottom temperature and 0.7 – 1.0 mmHg of reduced pressure under reflux ratio of 15 to give 482 g of the distillate, which was analyzed by gas chromatography. The result showed that the ratio of cisl-: trans-isomer was 98.4 : 1.6.

EXAMPLE 15 – 21

A mixture of cis- and trans-nerolidol in a ratio of 4 : 6 was subjected to rectification in the same manner as in Example 1 and the fore-running which was obtained on taking out trans-isomer was isomerized in the presence of several kinds of isomerization catalysts. After the reaction liquid was roughly distilled at 130° C of column bottom temperature, the distillate was again subjected to rectification to give trans-isomer. The results are shown in Table 2. In Example 16 and 19, the catalyst was distilled on rough-distillation, but it was separated as lower boiling part on further rectification.

Table 2

| Example | Ratio of cis-: trans-isomer in starting material | Catalyst | Conditions of isomerization | | Ratio of cis-: trans-isomer after isomerization | Yield* (%) |
|---|---|---|---|---|---|---|
| 15 | 68 : 32 | Ru (AA)₃ 0.4 wt. % | 160° C | 6 hrs. | 44 : 56 | 64 |
| 16 | 68 : 32 | 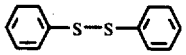 5 wt.% a small amount of BPO | 140° C | 7 hrs. | 47 : 53 | 59 |
| 17 | 70 : 30 |  5 wt. % | 140° C | 7 hrs. | 42 : 58 | 68 |
| 18 | 70 : 30 | Ru (AA)₃ 0.2 wt.% | 170° C | 8 hrs. | 52 : 48 | 43 |
| 19 | 70 : 30 |  5 wt. % a small amount of AIBN | 140° C | 6 hrs. | 43 : 57 | 62 |
| 20 | 65 : 35 | RuCl₂(PPh₃)₃ 0.5 wt. % | 160° C | 32 hrs. | 55 : 45 | 41 |
| 21 | 65 : 35 | WS₂ 0.4 wt. % | 180° C | 8 hrs. | 49 : 51 | 56 |

*The yield is that of trans-isomer obtained after separation of catalyst and rectification from the reaction mixture after isomerization.

EXAMPLE 22

In a 2-l. -three-necked flask was placed a mixture of 648 g. of ethyl orthoacetate, 440 g. of trans-nerolidol and 22 g. of isobutyric acid and the mixture was heated to 150° – 160° C. The reaction proceeded with a vigorous production of ethanol as a by-product which was continuously distilled off from the reaction system. The reaction product was analyzed by gas chromatography and disappearance of the starting alcohol indicated completion of the reaction. Isobutyric acid can be added further for more rapid reaction.

The reaction proceeded with a conversion of trans-nerolidol of not less than 95% and a selectivity to a mixture of $\Delta^4$-cis-$\Delta^8$-trans- and $\Delta^{4,8}$-trans-farnesylacetic acid ethyl esters of not less than 98%. After completion of the reaction, the reaction mixture as such was subjected to vacuum distillation without any after-treatment to afford 533 g. of the desired product in a pure state from distillates of b.p. 148° – 152° C. (0.4 mmHg). This product contained the cis- and trans-forms with respect to its $\Delta^4$-moiety in a proportion of 40 to 60.

The product thus obtained was subjected to distillation using a rectifying tower with number of theoretical plates of not less than 40 and a reflux ratio of 10 – 20 to afford 89 g. of ethyl $\Delta^4$-cis-, $\Delta^8$-trans-farnesylacetate from distillates of b.p. 126° – 128° C. (0.1 mmHg).

Its Refractive Index $n_d^{30} = 1.4708$

Figure 7:
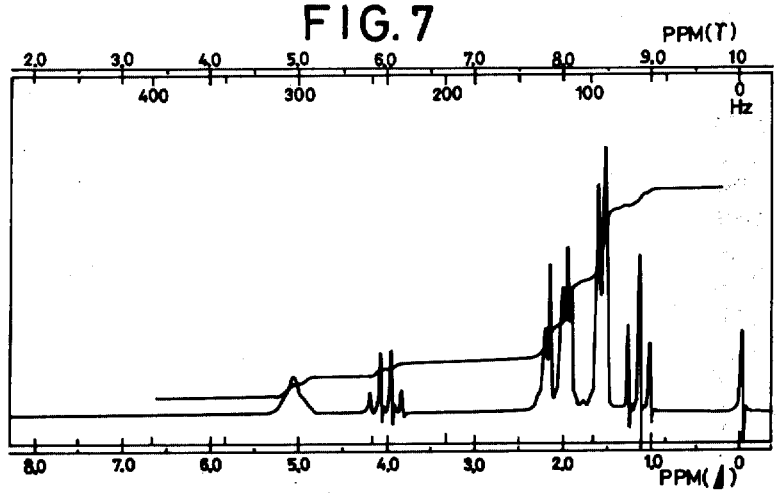

Its Nuclear Magnetic Resonance Spectrum in carbon tetrachloride as shown in FIG. 7.

198 g. of ethyl $\Delta^{4,8}$-trans-farnesylacetate was given from distillates of b.p. 130° – 132° C. (0.1 mmHg).

Its Refractive Index $n_D^{30} = 1.4708$

Figure 8:
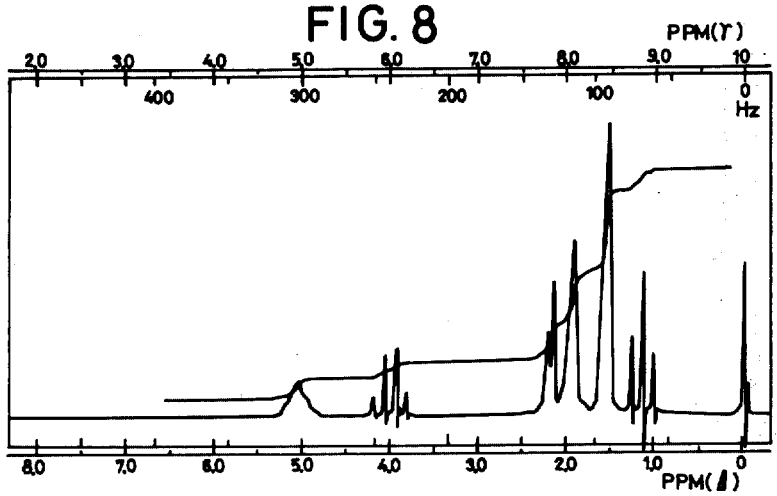

Its Nuclear Magnetic Resonance Spectrum in carbon tetrachloride as shown in FIG. 8.

Mass spectra of these products: $[M]^+ = 292$.

EXAMPLE 23

Following the same procedures as in Example 22, the reaction was conducted for 4 hours by heating 424 g. of ethyl orthoacetate, 314 lg. of cis-nerolidol and 5.2 g. of isobutyric acid to 150° – 160° C., while the ethanol formed in situ was continuously removed from the reaction system. Isobutyric acid as a catalyst should be supplemented at intervals since the acid was withdrawn from the reaction system. Disappearance of the starting material was confirmed by gas chromatography and vacuum distillation gave 344 g. of a mixture of ethyl $\Delta^{4,8}$-cis- and $\Delta^4$-trans- $\Delta^8$-cis-farnesylacetates from distillates of b.p. 143 – 148 C. (0.4 mmHg). This mixture contained the $\Delta^4$-cis- and $\Delta^4$-trans-forms in a proportion of about 40 to 60. Then, the mixture was distilled by means of a rectifying tower with number of theoretical plates of not less than 40 to give 42 g. of ethyl $\Delta^{4,8}$-cis-farnesylacetate from distillates of b.p. 142° – 144° C. (0.4 mmHg).

Its Refractive Index $n_D^{30} = 1.4703$

Its Nuclear magnetic RESONANCE Spectrum in carbon tetrachloride as shown in FIG. 9.

Further, 128 g. of ethyl $\Delta^4$-trans $\Delta^8$-cis-farnesylacetate was given from distillates of b.p. 146° – 148° C. (0.4 mmHg).

Its Refractive Index $n_D^{30} = 1.4708$

Its Nuclear Magnetic Resonance Spectrum in carbon tetrachoride as shown in FIG. 10.

Mass spectra of these compounds, $[M]^+ = 292$.

EXAMPLE 24

Following the same procedures as in Example 22, the reaction was conducted for 6 hours by heating a mixture of 592 g. of n-butyl orthoacetate, 220 g. of cis-nerolidol and 11 g. of hydroquinone to 160° – 165° C., while the n-butanol formed in situ was continuously removed from the reaction system. The reaction mixture as such was subjected to vacuum distillation to give 296 g. of n-butyl $\Delta^{4,8}$-cis- and $\Delta^4$-trans- $\Delta^8$-cis-farnesylacetate. The product was subjected to rectification to give 47 g. of n-butyl $\Delta^{4,8}$-cis-farnesylacetate from distillates of b.p. 133°– 135° C. (0.3 mmHg).

Its Refractive Index $n_D^{30} = 1.4695$

Figure 11:
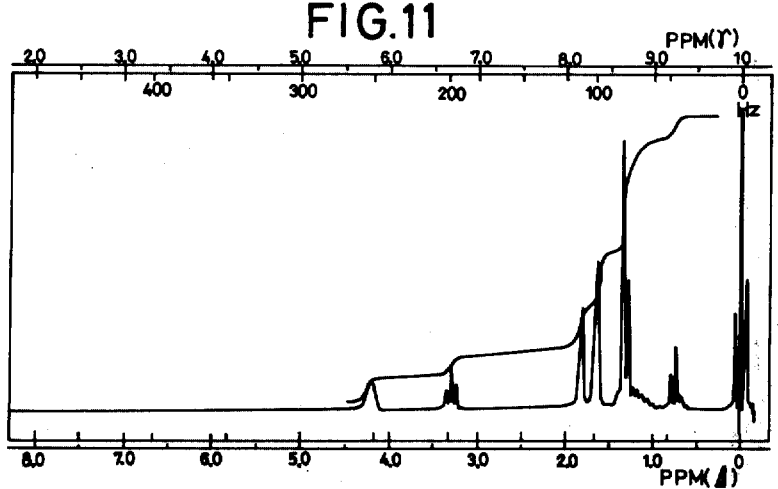

Its Nuclear Magnetic Resonance Spectrum in carbon tetrachloride as shown in FIG. 11.

Further, 414 g. of n-butyl $\Delta^4$-trans- $\Delta^8$-cis-farnesylacetate was given from distilltes of b.p. 135°–138° C. (0.3 mmHg).

Its Refractive Index $n_D^{30} = 1.4698$

Figure 12:
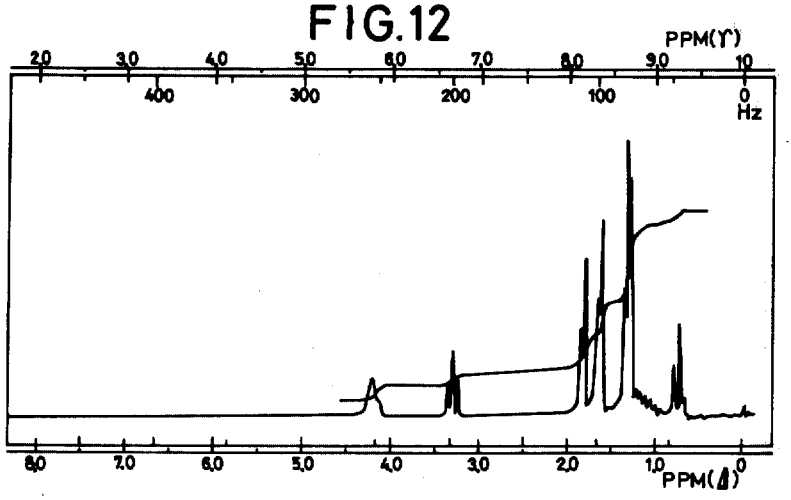

Its Nuclear Magnetic Resonance Spectrum in carbon tetrachloride as shown in FIG. 12.

EXAMPLE 25

Following the method reported by G. Pala et al. in Helv. Chim. Acta., 53, 1827 – 1832 (1970), a solution of 666 g. of trans-nerolidol, 2000 ml. of diethyl ether and 20 ml. of pyridine was cooled to −5° C – −10° C. and a solution of 300 g. of phosphorus tribromide in 500 ml. of diethyl ether was added gradually dropwise thereto at that temperature. After completion of the dropwise addition, the resulting mixture was stirred at that temperature for further 12 hours. After completion of the reaction, the reaction mixture was poured into water and neutralized with sodium hydrogen carbonate. The ether layer was washed with water and dried over anhydrous sodium sulfate. The solvent was distilled off at room temperature under reduced pressure to give 760 g. of farnesyl bromide with reddish yellow color and irritative odor. This product should be employed as such without any further purification or be kept in a cold place.

Then, a condensation reaction was effected by the use of 501 g. of the so obtained farnesyl bromide and 285 g. of diethyl malonate in 1500 ml. of ethanol in the presence of 37.1 g. of metallic sodium. The reaction mixture was poured into water and extracted with ether. The ether extract was dried over anhydrous sodium sulfate and the solvent was distilled off. The residue was subjected to vacuum distillation to give 378 g. of diethyl farnesylmalonate from a distillate of b.p. 158°– 160° C. (0.2 mmHg). The ester was then saponified and decarboxylated with 204 g. of potassium hydroxide in 1000 ml. of ethanol, neutralized with aqueous hydrochloric acid and then extracted with ether. After removing the ether, the residue was subjected to vacuum distillation to give 218 g. of a mixture of $\Delta^8$-trans- $\Delta^4$-cis- and trans-farnesylacetic acids from distillates of b.p. 147° – 150° C. (0.2 mmHg). The product was subjected to fractional distillation by means of a rectifying tower with a number of theroretical plates of not less than 40 to give 33 g. of $\Delta^4$-cis- $\Delta^8$-trans-farnesylacetic acid and 87 g. of $\Delta^{4,8}$-trans-farnesylacetic acid from distillates of b.p. 146° – 147° C. (0.2 mmHg) and of b.p. 147° – 149° C. (0.2 mmHg), respectively.

EXAMPLE 26

In a 2-l. three-necked flask was placed a mixture of 648 g. of ethyl orthoacetate, 440 g. of nerolidol and 22 g. of isobutyric acid, which was then heated at 150° – 160° C. Since the reaction was accompanied by a vigorous side-reaction to produce ethanol, the ethanol was continuously removed from the reaction system. Progress of the reaction was checked by gas chromatography and the reaction should be discontinued at the point of disappearance of the starting nerolidol. In order to accelerate the reaction, a further amount of isobutyric acid can be added. The reaction gave more than 95% of the conversion ratio based on the amount of nerolidol and more than 98% of the selectivity to ethyl farnesylacetate. The reaction mixture was distilled in vacuo without any post-treatment to give 533 g. of the desired product, b.p. 145° – 152° C (0.4 mmHg). The result of gas chromatographic analysis showed that this substance was a mixture of stereo-isomers, 15% of $\Delta^{4,8}$-cis-isomer, 47% of $\Delta^4$-cis- $\Delta^8$-trans- and $\Delta^4$-trans- $\Delta^8$-cis-isomers, and 38% of $\Delta^{4,8}$-trans-isomer. Then, the mixture was fractionated through a rectifying column with 40 theoretical plates, which was operated under the conditions of 175° – 185° C bottom temperature and 10-20 reflux ratio, to give 150.0 g. of ethyl $\Delta^{4,8}$-trans-farnesylacetate, b.p. 130° – 132° C (0.1 mmHg).

Refractive index: $n_D^{30} = 1.4708$

Figure 21:
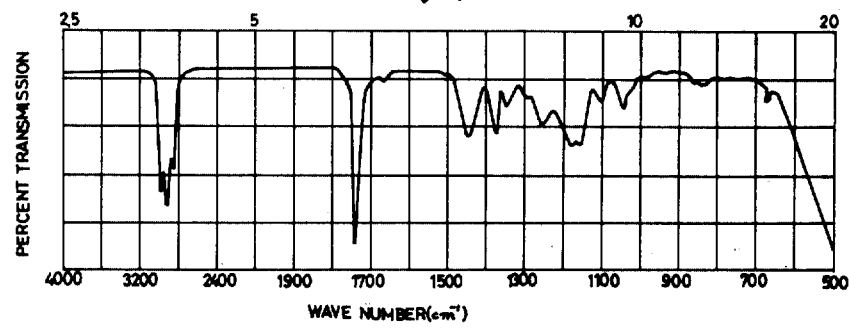

NMR and IR spectra are shown in FIG. 8 and FIG. 21, respectively. The molecular ion (parent ion) peak $[M]^+$ was shown at 292 in mass spectrum.

To 362 g. of ethyl farnesylacetate obtained at the first distillate on rectification, which was composed of 22.1% of $\Delta^{4,8}$-cis-isomer, 69.2% of $\Delta^4$-cis- $\Delta^8$-trans- and $\Delta^4$-trans- $^8$-cis-isomers, and 8.7% of $\Delta^{4,8}$-trans-isomer, was added 11 g. of phenyldisulfide and a small amount of an radical initiator, azobisisobutyronitrile (AIBN for short, hereinafter), and the mixture was heated for 24 hours at 140° C in a nitrogen atmosphere. After reaction, the above mentioned ratio was 16.9 : 50.7: 32.4 by gas chromatography. The reaction mixture, was roughly distilled in about 0.1 mmHg to give 356 g. of the distillate. Subsequently, this was fractionated through a rectifying column with 40 theoretical plates to give 237.8 g. of the first distillate and b 84.2 g. of the second distillate, ethyl $\Delta^{4,8}$-trans-farnesylacetate.

EXAMPLE 27

Following the same procedures as in Example 26, a mixture of 1184 g. of n-butyl orthoacetate, 220 g. of nerolidol and 22 g. of hydroquinone was reacted with heating at 160° – 165° C, with removal of n-butanol produced from the reaction system. The reactin mixture was directly distilled in vacuo to give 598 g of n-butyl farnesylacetate, b.p. 134° – 142° C (0.3 mmHg). Then, this product was fractionated through a rectifying column with 40 numbers of theoretical plates reflux ratio of 20 to give 147.5 g of n-butyl $\Delta^{4,8}$-trans-farnesylacetate, b.p. 140° – 142° C (0.3 mmHg). 64% of $\Delta^{4,8}$-trans-isomer introduced was recovered on distillation.

To 437.5 g of n-butyl farnesylacetate obtained as the first distillate on rectification, which is composed of 21.9% of $\Delta^{4,8}$-cis-isomer, 65.6% of $\Delta^4$-cis- $\Delta^8$-trans-isomer and $\Delta^4$-trans- $\Delta^8$-cis-isomer, and 12.5% of $\Delta^{4,8}$-trans-isomer, 21.8 g of thiophenol and a small amount of benzoyl peroxide were added. The mixture was heated for 24 hours at 140° C in a nitrogenous atmosphere. The reaction mixture was analyzed by gas chromatography to show that the above-mentioned ratio of isomers was 16.3 : 48.8 : 34.9. The product was directly distilled roughly at the bottom temperature of 150° – 160° C in 0.1 mmHg to give 418.8 g of a distillate. Subsequently, the distillate was fractionated through a rectifying column with about 40 theoretical plates to give 308.8 g of the first distillate and 97.4 g of the second distillate, n-butyl farnesylacetates. To 308.8 g of the above-mentioned first distillate, which is a mixture of 22.1% of $\Delta^{4,8}$-cis-isomer, 66.2% of $\Delta^4$-cis- $\Delta^8$-trans- and $\Delta^4$-trans-$\Delta^8$-cis-isomers, and 11.7% of $\Delta^{4,8}$-trans-isomer, 15.5 g of thiophenyl and a small amount of benzoyl peroxide were added. The mixture was submitted to isomerization by heating it for 24 hours at 140° C in a nitrogen atmosphere. The reaction mixture was given in a ratio of 16.4 : 49.2 : 34.4. The mixture was roughly distilled to give 299 g of a distillate, which was further fractionated to give 222 g of the first distillate and 66 g of the second distillate, $\Delta^{4,8}$-trans-isomer.

EXAMPLE 28

Following the procedure reported by G. Pala et al. in Helv. Chim. Acta., 53, 1827 – 1832 (1970), a mixture of 666 g of nerolidol (cis : trans = 40 : 60), 2,000 ml of diethyl ether and 20 ml of pyridine was cooled at −5° – 10° C. Thereto, 300 g of phosphorus tribromide was added dropwise slowly at the same temperature. Thereafter, the reaction was completed by further stirring of the mixture for 12 hours at the same temperature. The reaction mixture was poured into water and neutralized with sodium bicarbonate. The ether layer was washed with water and dried over anhydrous sodium sulfate. The solvent was distilled off in vacuo at room temperature to give 760 g of farnesyl bromide which showed orange color and irritating odor. As this substance was relatively unstable, it was brought to the following reaction without further purification or kept in a cold place.

Then, 501 g of farnesyl bromide as mentioned above and 285 g of diethyl malonate in 1,500 ml of ethanol were subjected to a condensation reaction in the presence of 37.1 g of metallic sodium. The reaction mixture was poured into water and extracted with ether. The organic layer was dried over anhydrous sodium sulfate. After removing the solvent, the residue was fractionated in vacuo to give 378 g of diethyl farnesylmalonate, b.p. 155° – 160° C (0.2 mmHg). This product was saponified and decarboxylated in 1,000 ml of ethanol with 204 g of potassium hydroxide. The reaction mixture was neutralized with hydrochloric acid and extracted with ether. After removing the solvent, the residue was fractionated in vacuo to give 218 g of farnesylacetic acid, b.p. 142° – 150° C (0.2 mmHg). the gas chromatographic analysis using 5% of polyethylene glycol 20 M (GE-20M. for short) on kieselguhr (60 – 80 mesh) at 180° C of the column temperature, indicated that the substance was a mixture of stereo-isomers, 16% of $\Delta^{4,8}$-cis-isomer, 48% of $\Delta^4$-cis-$\Delta^8$-trans- and $\Delta^4$-trans-$\Delta^8$-cis-isomers, and 36% of $\Delta^4$-trans-$\Delta^8$-trans-isomer. By further fractionation through a rectifying column with 40 theoretical plates, was obtained 56.6 g of $\Delta^{4,8}$-trans-farnesylacetic acid, b.p. 147° – 149° C (0.2 mmHg). This showed that the $\Delta^{4,8}$-trans-isomer was recovered in a yield of 72% based on the amount contained in the mixure. subsequently, 150 g of farnesylacetic acid, which was obtained as the first distillate, was isomerized by heating with 0.15 g of acetylacetonatoruthenium $R_U$ (AA)$_3$ at 200° C in a nitrogenous atmosphere. By gas chromatographic analysis, the ratio of $\Delta^{4,8}$-cis-isomer, $\Delta^4$-cis-$\Delta^8$-trans-isomer + $\Delta^4$-trans-$\Delta^8$-cis-isomer and $\Delta^{4,8}$-trans-isomer was 23.3 : 69.7 : 7.0 in the starting farnesylacetic acid and was 17.7 : 52.9 : 29.4 after isomerization.

The reaction mixture was roughly distilled without further treatment at the bottom temperature of 150° – 160° C in 0.05 – 0.1 mmHg to give 145.2 g of a distillate. The above-mentioned ratio of the isomers was 18.3 : 54.7 : 27.0 by gas chromatographic analysis.

Since the ratio of the isomers was not changed after heating at 200° C for 4 hours, it was confirmed that the catalyst, $R_u$ (AA)$_3$ was not distilled out of the still. Then, the distillate obtained above was fractionated through a rectifying column with about 40 theoretical plates to give 124 g of the first distillate and 26.7 g of the second distillate, $\Delta^{4,8}$-trans-farnesylacetic acid.

EXAMPLE 29 – 31

In Table 3 are shown results of the fractionation of several farnesylacetates, which was carried out at 10 – 20 reflux ratio through a rectifying column with forty theoretical plates.

EXAMPLE 32 –38

Following the same procedures as in Example 26, the first distillate, which was obtained when separating the desired $\Delta^{4,8}$-trans-isomer of farnesylacetates, was submitted to isomerization reaction by heating in the presence of several kinds of catalyst. The reaction mixture was roughly distilled at the bottom temperature of 150° – 180° C and the distillate was further rectified to give $\Delta^{4,8}$-trans-isomers.

Results are shown in Table 4.

Table 3

| Example | R in 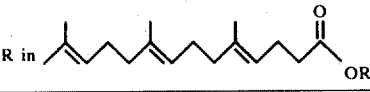 OR | Composition* | Recovery (%) by distillation | Boiling point* |
|---|---|---|---|---|
| 29 | CH₃— | 20 : 60 : 20 | 84.2 | 127 – 129° C (0.2 mmHg) |
| 30 | 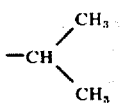 | 16 : 48 : 36 | 77.6 | 146 – 148° C (0.2 mmHg) |
| 31 | 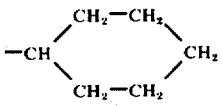 | 16 : 48 : 36 | 58.3 | 171 – 173° C (0.2 mmHg) |

\* : Composition, ($\Delta^{4,8}$-cis-isomer): ($\Delta^4$-trans-$\Delta^8$-cis-isomer + $\Delta^4$-cis-$\Delta^8$-trans-isomer) : ($\Delta^{4,8}$-trans-isomer), analyzed by gas chromatography.
\*\* : Recovery from $\Delta^{4,8}$-trans-isomer introduced.
\*\*\* : Boiling Point of $\Delta^{4,8}$-trans-isomer.

Table 4

| Example | R—* | Ratio of isomers** before isomerization | Catalyst | Reaction condition | Ratio of** isomers after isomerization | Boiling*** point | Yield**** in per cent |
|---|---|---|---|---|---|---|---|
| 32 | CH₃— | 23.4:70.3:6:3 | Ru (AA)₃ 0.2 wt. % | 180° C 8 hrs | 17.5:52.3:30.2 | 117–119° C (0.1 mmHg) | 78.3 |
| 33 | CH₃— | 23.7:71.1:5.2 | 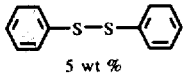 5 wt % a small amount of BPO | 140° C 24 hrs | 16.:48.1:35.8 | " | 84.6 |
| 34 | C₂H₅— | 23.2:69.5:7.3 |  5 wt % a small amount of AIBN | " | 16.1:48.2:35.7 | 125–127° C (0.1 mmHg) | 74.5 |
| 35 | n-C₃H₇— | 23.1:69.1:7.8 | Rᵤ (AA)₃ 0.2 wt % | 190° C 15 hrs | 17.1:51.5:31.4 | 136–138° C (0.1 mmHg) | 70.7 |
| 36 | n-C₃H₇— | 23.0:69.0:8.0 | 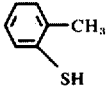 5 wt % a small amount of AIBN | 140° C 24 hrs | 16.3:49.0:34.7 | " | 71.2 |
| 37 | n-C₃H₇— | 22.9:68.7:8.4 | RuCl₂(PPh₃)₃ 0.5 wt % | 170° C 48 hrs | 18.0:54.1:27.9 | " | 67.8 |
| 38 | n-C₄H₉— | 24.4:65.0:10.6 | WS₂ | 190° C | 18.9:56.8:24.3 | 131–132° C | 65.9 |

Table 4-continued

| Example | R—* | Ratio of isomers** before isomerization | Catalyst | Reaction condition | Ratio of** isomers after isomerization | Boiling*** point | Yield**** in per cent |
|---|---|---|---|---|---|---|---|
| | | | 0.4 wt % | 8 hrs | | (0.1 mmHg) | |

\* : R in the formula (1).
\*\* : Ratio of ($\Delta^{4,8}$-cis-isomer) : ($\Delta^4$-cis-$\Delta^8$-trans-isomer + $\Delta^4$-trans-$\Delta^8$-cis-isomer) : ($\Delta^{4,8}$-trans-isomer).
\*\*\* : The boiling point of $\Delta^{4,8}$-trans-isomers.
\*\*\*\* : The yield based on $\Delta^{4,8}$-trans-isomer contained in the reaction mixture.

EXAMPLE 39 – 42

To the $\Delta^{4,8}$-cis- or $\Delta^4$-trans-$\Delta^8$-cis- or $\Delta^4$-cis-$\Delta^8$-trans- or $\Delta^{4,8}$-trans-farnesylacetic acid ethyl ester obtained in Example 22 or 23 was added 0.1 – 10 mole % of sodium hydroxide or potassium hydroxide and the resulting mixture was heated with 1.5 - 2 times moles of geraniol in toluene or xylene to effect a transesterification reaction. After completion of the reaction, the solvent was distilled off and the residue was subjected to high vacuum distillation to give stereospecific farnesylacetic acid geranyl in yields of 75 – 85%, respectively.

The results are listed in the following Table 5 and they are consistent with those shown by G. Pata et al. in Helv. Chim. Acta., 53, 1827 (1970).

Table 5

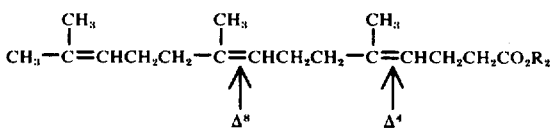

Figure 13:
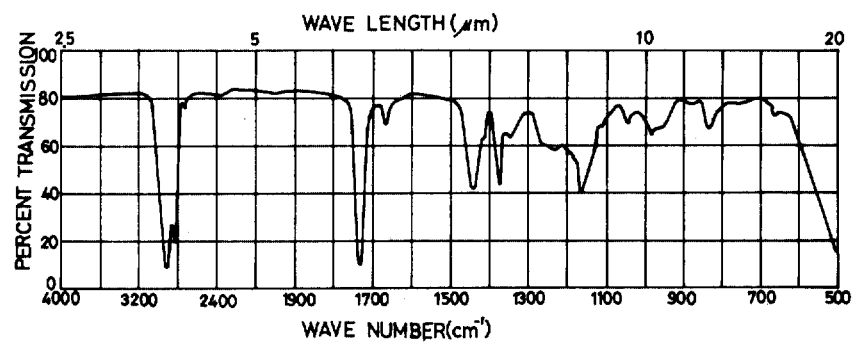
Figure 14:
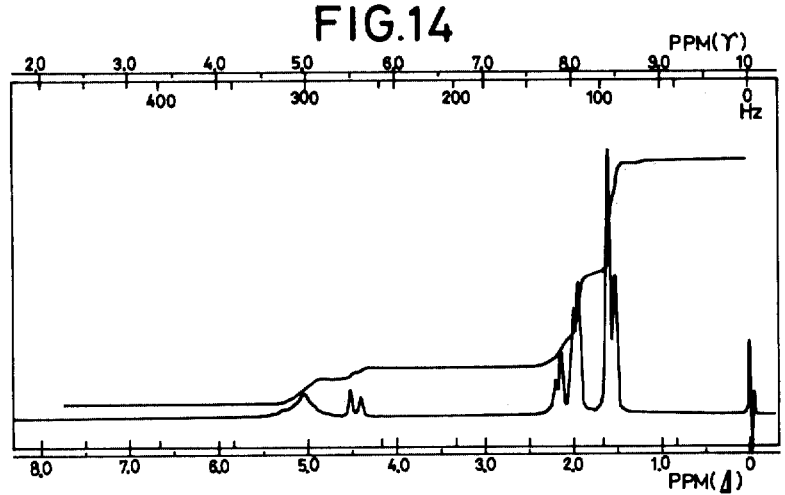
Figure 15:
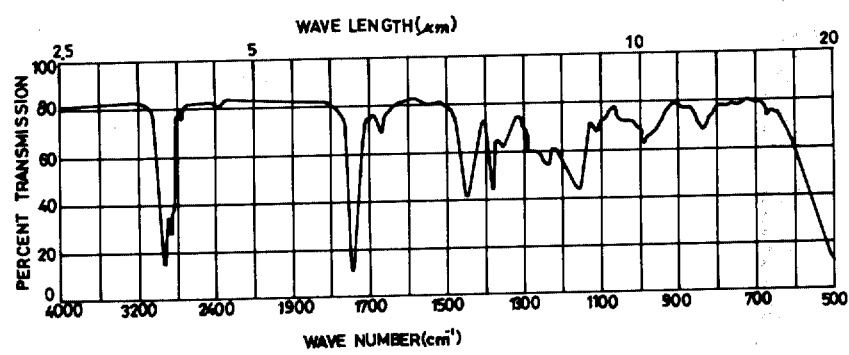
Figure 16:
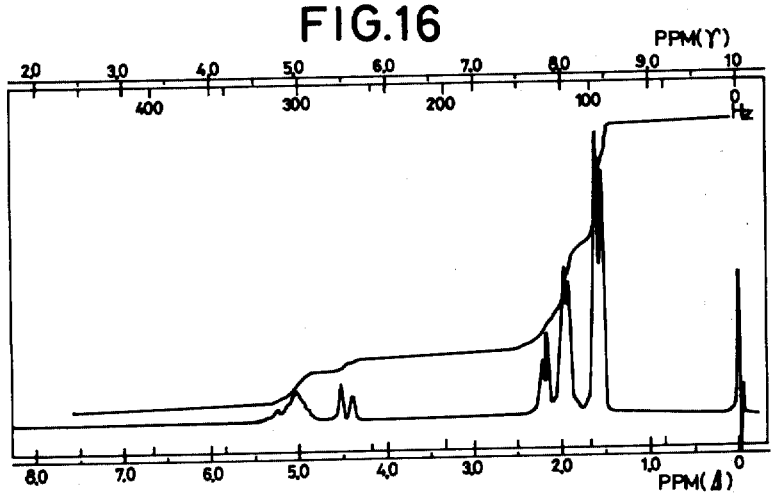
Figure 17:
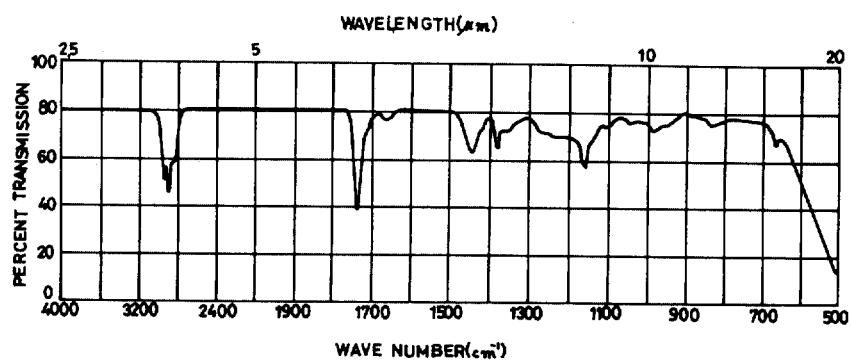
Figure 18:
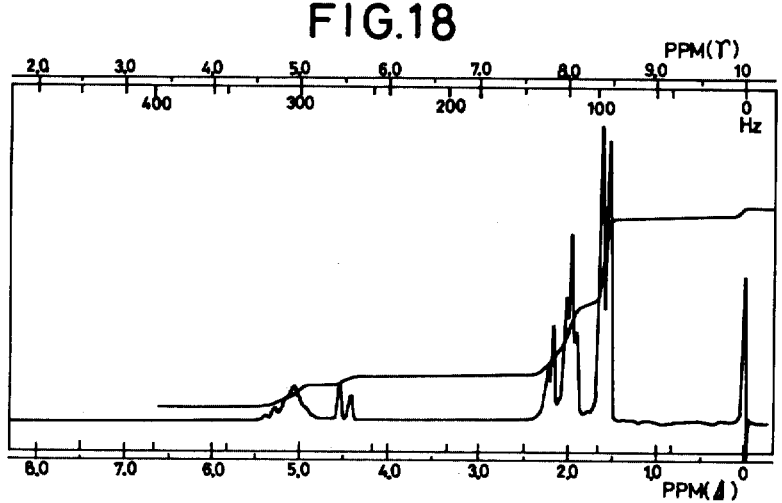

| Example | | b.p. (° C, 0.1 mmHg) | $n_D^{30}$ | IR spectrum | NMR spectrum |
|---|---|---|---|---|---|
| 39 | $^{4,8}$-cis- | 190 – 195 | 1.4870 | FIG. 13 | FIG. 14 |
| 40 | $^4$-tran- $^8$-cis- | 193 – 198 | 1.4872 | FIG. 15 | FIG. 16 |
| 41 | $^4$-cis-$^8$-trans- | 197 – 203 | 1.4869 | FIG. 17 | FIG. 18 |
| 42 | $^{4,8}$-trans- | 201 – 206 | 1.4878 | FIG. 19 | FIG. 20 |

*Ge represents a geranyl radical.

EXAMPLE 43

$\Delta^{4,8}$-trans-farnesylacetic acid, which was obtained in Example 28, and two times the amount thereof of geraniol were refluxed in benzene or toluene for 8 hours in the presence of 0.1 – 0.2 mole % of p-toluene-sulfonic acid as a catalyst. Water liberated was removed contiuously from the reaction system. Then the organic layer was washed three times with an aqueous solution saturated with sodium bicarbonate and dried over anhydrous sodium sulfate. After distilling off the solvent, the residue was fractionated under reduced pressure to give geranyl ester of farnesylacetic acid, b.p. 201° – 206° C (0.1 mmHg) in 65 – 75% yield.

Refractive index of this compound: $n_D^{30} = 1.4878$

Figure 19:
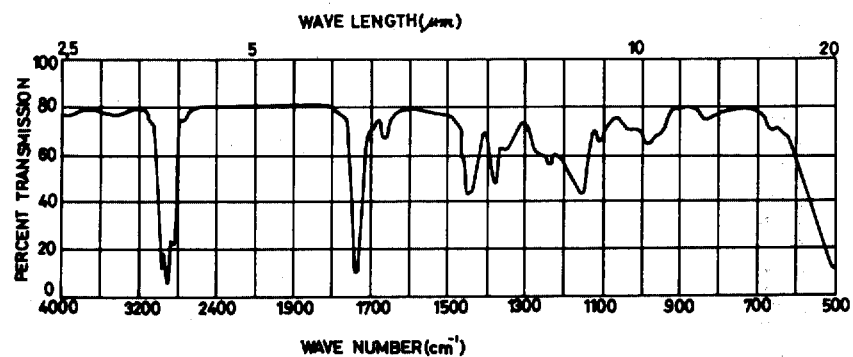
Figure 20:
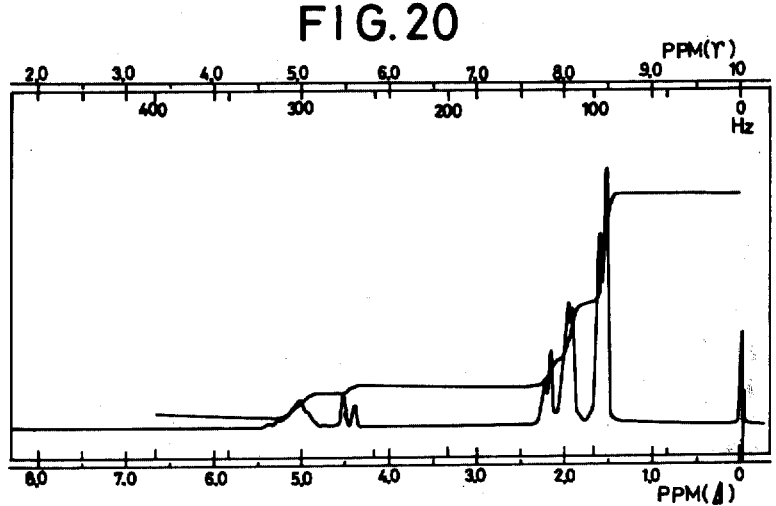

NMR and IR spectra are shown in FIG. 20 and FIG. 19, respectively.

What is claimed is:

1. A process for preparing a stereospecific farnesylacetic acid or ester thereof, at $\Delta^4$ and $\Delta^8$ positions, having the formula:

$$\underset{\Delta^8}{\uparrow} \underset{\Delta^4}{\uparrow}$$
CH$_3$—C=CHCH$_2$CH$_2$—C=CHCH$_2$CH$_2$—C=CHCH$_2$CH$_2$CO$_2$R$_2$
with CH$_3$ groups on each =C.

wherein R$_2$ represents hydrogen atom, a lower alkyl radical having 1 to 6 carbon atoms, a lower cycloalkyl radical having 3 to 6 carbon atoms, a lower alkenyl radical having 2 to 6 carbon atoms or a lower cycloalkenyl radical having 3 to 6 carbon atoms, which comprises rectifying a stereo isomeric mixture of farnesylacetic acids or esters thereof in a rectification column having from 10 to 100 theroretical plates and with a reflux ratio of from 2 to 100; said stereo isomeric mixture being one of the following mixtures:

i. a mixture of $\Delta^{4,8}$-cis- and $\Delta^4$-trans-$\Delta^8$-cis-farnesylacetic acids or esters thereof,
ii. a mixture of $^{4,8}$-trans- and $^4$-cis-$^8$-trans-farnesylacetic acids or esters thereof, or
iii. a mixture of four isomers of $\Delta^{4,8}$-cis-, $\Delta^4$-trans-$\Delta^8$-cis-, $\Delta^4$-cis-$\Delta^8$-trans- and $\Delta^{4,8}$-trans-farnesylacetic acids or esters thereof, to separate each stereospecific farnesylacetic acid or ester thereof from the mixture of (i) or (ii), or to separate $\Delta^{4,8}$-trans- or $\Delta^{4,8}$-cis-farnesylacetic acid or ester thereof from the mixture of (iii).

2. The process according to claim 1, wherein said rectification of the mixture is conducted under a reduced pressure and a bottom temperature below 280° C.

3. The process according to claim 1, wherein said rectification of the mixture is conducted by using a rectification column having from 20 to 60 theoretical plates and with a reflux ratio of from 5 to 30.

4. The process for preparing $\Delta^{4,8}$-trans-farnesylacetic acid or ester thereof according to claim 1, wherein said mixture is a mixture of (iii) described in claim 1.

5. The process for preparing $\Delta^{4,8}$-trans-farnesylacetic acid or ester thereof according to claim 1, which comprises:

1. rectifying a mixture of (iii) of claim 1 to obtain $\Delta^{4,8}$-trans-farnesylacetic acid or ester thereof as the after fraction distillate;
2. isomerizing the fore-running distillate, which comprises a mixture of $\Delta^{4,8}$-cis-, $\Delta^4$-trans-$\Delta^8$-cis-, and $\Delta^4$-cis-$\Delta^8$-trans-farnesylacetic acids or esters thereof, or the mixture of said three isomers and a minor amount of $\Delta^{4,8}$-trans-farnesylacetic acid or ester thereof, in the presence of an isomerization catalyst to isomerize said three isomers in the fore-running distillate into $\Delta^{4,8}$-isomer; and
3. re-rectifying said isomerized fore-running distillate to recover $\Delta^{4,8}$-trans-farnesylacetic acid or ester thereof.

6. The process according to claim 5, wherein said isomerization catalyst is a compound of a transition metal from Group VI, VII, or VIII of the Periodic Table, or an organic sulfur compound.

7. The process according to claim 5, wherein said isomerization catalyst contains ruthenium.

8. The process according to claim 5, wherein said isomerization catalyst contains tungsten.

9. The process according to claim 5, wherein said isomerizing catalyst is an organic sulfur compound.

10. The process according to claim 1, wherein said mixture is a mixture of (i) or (ii).

11. A process for preparing a stereospecific farnesylacetic acid ester, at $\Delta^4$ and $\Delta^8$ positions, having the formula:

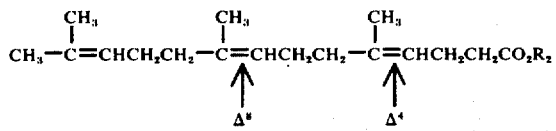

wherein $R_1$ represents a lower alkyl radical having 1 to 6 carbon atoms, a lower cycloalkyl radical having 3 to 6 carbon atoms, a lower alkenyl radical having 2 to 6 carbon atoms, or a lower cycloalkenyl radical having 3 to 6 carbon atoms, which comprises:
1. rectifying a mixture of $\Delta^6$-cis- and $\Delta^6$-trans-nerolidols to separate each one of them,
2. reacting said $\Delta^6$-cis- or $\Delta^6$-trans-nerolidol with an orthoacetic acid ester having the formula $$CH_3C(OR_1)_3$$

wherein $R_1$ is the same as described above, in the presence of an acidic catalyst to produce
   i. a mixture of $\Delta^{4,8}$-cis- and $\Delta^4$-trans-$\Delta^8$-cis-farnesylacetic acid ester from $\Delta^6$-cis-nerolidol, or
   ii. a mixture of $\Delta^{4,8}$-trans- and $\Delta^4$-cis-$\Delta^8$-trans-farnesylacetic acid ester from $\Delta^6$-trans-nerolidol, and
3. rectifying said mixture (i) or (ii) to separate each one of said isomers, respectively.

12. The process according to claim 11, wherein said stereospecific nerolidols are obtained by subjecting $\Delta^5$-cis-gernaylacetone or $\Delta^5$-trans-geranylacetone to vinylation to form $\Delta^6$-cis-nerolidol from $\Delta^5$-cis-geranylacetone and to form $\Delta^6$-trans-nerolidol from $\Delta^5$-trans-geranylacetone.

13. The process according to claim 12, wherein said $\Delta^5$-cis- or $\Delta^5$-trans-geranylacetone is produced by rectifying the mixture of said stereo isomeric geranylacetones.

14. The process according to claim 11, wherein said stereospecific nerolidols are obtained by subjecting $\Delta^5$-cis-geranylacetone or $\Delta^5$-trans-geranylacetone to ethynylation and then partial hydrogenation to form $\Delta^6$-cis-nerolidol from $\Delta^5$-cis-geranylacetone and to form $\Delta^6$-trans-nerolidol from $\Delta^5$-trans-geranylacetone.

15. The process according to claim 13, wherein said $\Delta^5$-cis- or $\Delta^5$-trans-geranylacetone is produced by rectifying the mixture of said stereo isomeric geranylacetone.

* * * * *